(12) United States Patent
Kubo et al.

(10) Patent No.: US 10,553,904 B2
(45) Date of Patent: Feb. 4, 2020

(54) ELECTROLYTE SOLUTION FOR NON-AQUEOUS ELECTROLYTE BATTERY, AND NON-AQUEOUS ELECTROLYTE BATTERY USING THE SAME

(71) Applicant: CENTRAL GLASS CO., LTD., Yamaguchi (JP)

(72) Inventors: Makoto Kubo, Ube (JP); Takayoshi Morinaka, Ube (JP); Mikihiro Takahashi, Ube (JP); Masutaka Shinmen, Sanyoonoda (JP); Wataru Kawabata, Ube (JP); Hiroki Matsuzaki, Ube (JP)

(73) Assignee: CENTRAL GLASS CO., LTD., Yamaguchi (JP)

( * ) Notice: Subject to any disclaimer, the term of this patent is extended or adjusted under 35 U.S.C. 154(b) by 0 days.

(21) Appl. No.: 15/549,210

(22) PCT Filed: Feb. 18, 2016

(86) PCT No.: PCT/JP2016/054748
§ 371 (c)(1),
(2) Date: Aug. 7, 2017

(87) PCT Pub. No.: WO2016/133169
PCT Pub. Date: Aug. 25, 2016

(65) Prior Publication Data
US 2018/0034103 A1 Feb. 1, 2018

(30) Foreign Application Priority Data

Feb. 19, 2015 (JP) .................. 2015-030411
Dec. 25, 2015 (JP) .................. 2015-254114

(51) Int. Cl.
| | |
|---|---|
| *H01M 10/0567* | (2010.01) |
| *H01M 10/0568* | (2010.01) |
| *C07F 9/28* | (2006.01) |
| *C07C 317/24* | (2006.01) |
| *C07F 9/02* | (2006.01) |
| *H01M 10/0569* | (2010.01) |
| *H01M 10/0525* | (2010.01) |
| *H01M 10/054* | (2010.01) |

(52) U.S. Cl.
CPC ....... *H01M 10/0567* (2013.01); *C07C 317/24* (2013.01); *C07F 9/02* (2013.01); *C07F 9/28* (2013.01); *H01M 10/054* (2013.01); *H01M 10/0525* (2013.01); *H01M 10/0568* (2013.01); *H01M 10/0569* (2013.01); *H01M 2220/20* (2013.01); *H01M 2220/30* (2013.01); *H01M 2300/0028* (2013.01)

(58) Field of Classification Search
CPC .......... H01M 10/0525; H01M 10/054; H01M 10/0567; H01M 10/0568; H01M 10/0569; H01M 2220/20; H01M 2220/30; H01M 2300/0028; C07C 317/24; C07F 9/02; C07F 9/28

USPC ...................................... 429/231.1
See application file for complete search history.

(56) References Cited

U.S. PATENT DOCUMENTS

| | | |
|---|---|---|
| 5,885,733 A | 3/1999 | Ohsawa et al. |
| 2002/0012850 A1 | 1/2002 | Schmidt et al. |
| 2002/0112850 A1 | 1/2002 | Schmidt et al. |
| 2002/0076619 A1 † | 6/2002 | Yamada |
| 2004/0007688 A1 | 1/2004 | Awano et al. |
| 2010/0015514 A1 | 1/2010 | Miyagi et al. |
| 2010/0323240 A1 | 12/2010 | Tsujioka et al. |

(Continued)

FOREIGN PATENT DOCUMENTS

| | | |
|---|---|---|
| CN | 106471000 | 3/2017 |
| EP | 3 165 528 | 5/2017 |

(Continued)

OTHER PUBLICATIONS

International Search Report dated May 10, 2016 in International (PCT) Application No. PCT/JP2016/054748.
Denmark et al., "Silicon-Directed Nazarov Cyclizations-IV, Further Studies in Stereochemical Control", Tetrahedron, vol. 42, No. 11, 1986, pp. 2821-2829.

(Continued)

*Primary Examiner* — Amanda C. Walke
(74) *Attorney, Agent, or Firm* — Wenderoth, Lind & Ponack, L.L.P.

(57) ABSTRACT

The present invention provides an electrolyte solution for a non-aqueous electrolyte battery capable of an exerting high average discharge voltage and an excellent low-temperature output characteristic at −30° C. or lower and an excellent cycle characteristic and an excellent storage characteristic at high temperatures of 50° C. or higher, as well as a non-aqueous electrolyte battery containing the same. The present electrolyte solution comprises a non-aqueous solvent, a solute, at least one silane compound represented by the following general formula (1) as a first compound, and a fluorine-containing compound represented by the following general formula (3), for example, as a second compound.

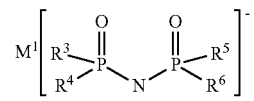

13 Claims, No Drawings

(56) References Cited

U.S. PATENT DOCUMENTS

| | | |
|---|---|---|
| 2013/0022861 A1 | 1/2013 | Miyagi et al. |
| 2014/0080010 A1 | 3/2014 | Tode et al. |
| 2014/0193706 A1 | 7/2014 | Morinaka et al. |
| 2015/0243936 A1 | 8/2015 | Miyagi et al. |
| 2017/0040593 A1 | 2/2017 | Miyagi et al. |
| 2017/0204124 A1* | 7/2017 | Takahashi ............ H01M 10/052 |
| 2017/0222264 A1* | 8/2017 | Morinaka ............ H01M 10/052 |

FOREIGN PATENT DOCUMENTS

| | | | |
|---|---|---|---|
| JP | 8-78053 | 3/1996 | |
| JP | 10-139784 | 5/1998 | |
| JP | 2000-123867 | 4/2000 | |
| JP | 2002-33127 | 1/2002 | |
| JP | 2002-134169 | 5/2002 | |
| JP | 2004-39510 | 2/2004 | |
| JP | 2004-87459 | 3/2004 | |
| JP | 2007-149656 | 6/2007 | |
| JP | 2008-004349 | 1/2008 | |
| JP | 2008-181831 | 8/2008 | |
| JP | 2008-222484 | 9/2008 | |
| JP | 2013-30465 | 2/2013 | |
| JP | 2013-51122 | 3/2013 | |
| JP | 2014-35929 | 2/2014 | |
| KR | 2012-0104759 | 9/2012 | |
| KR | 20120104759 A † | 9/2012 | |
| KR | 20140040283 A † | 4/2014 | |
| WO | WO-2016002774 A1 * | 1/2016 | .......... H01M 10/052 |
| WO | WO-2016017404 A1 * | 2/2016 | .......... H01M 10/052 |

OTHER PUBLICATIONS

Hood et al., "Esters of Monofluorophosphoric Acid", Journal of the American Chemical Society, vol. 72, Nov. 1950, pp. 4956-4958.

Alkherraz et al., "Phosphate ester analogues as probes for understanding enzyme catalysed phosphoryl transfer", Faraday Discussions, vol. 145, 2010, pp. 281-299.

Office Action dated Sep. 28, 2018 in corresponding Korean Patent Application No. 10-2017-7026392, with English translation.

Notice of Reasons for Refusal dated Jun. 24, 2019 in Japanese Patent Application No. 2015-254114, with English Translation.

\* cited by examiner
† cited by third party

ELECTROLYTE SOLUTION FOR NON-AQUEOUS ELECTROLYTE BATTERY, AND NON-AQUEOUS ELECTROLYTE BATTERY USING THE SAME

TECHNICAL FIELD

The present invention relates to an electrolyte solution for a non-aqueous electrolyte battery comprising a specific silane compound and a salt having a fluorophosphoryl structure and/or a fluorosulfonyl structure, as well as a non-aqueous electrolyte battery containing the electrolyte solution.

BACKGROUND ART

In recent years, power storage systems to be applied for small apparatuses that need high energy density, such as information technology-related apparatuses or communication apparatuses, specifically, personal computers, video cameras, digital still cameras, and cell phones, and power storage systems to be applied for large apparatuses that need power, such as electric vehicles, hybrid vehicles, auxiliary power for fuel cell vehicles, and energy storage have received attention. As a candidate therefor, non-aqueous electrolyte batteries such as a lithium ion battery, a lithium battery, a lithium ion capacitor, or a sodium ion battery, have been actively developed.

Many of these non-aqueous electrolyte batteries have already been put into practical use, but none of these batteries has satisfactory properties for use in various applications. In particular, a non-aqueous electrolyte battery to be mounted on a vehicle such as an electric vehicle is required to have a high input output characteristic even in a cold season. Hence, improvement in a low-temperature characteristic is important. In addition to the low-temperature characteristic, such a battery is required to have a high-temperature cycle characteristic such that reduction in capacity is small even when charging and discharging are performed repeatedly under a high temperature environment (a high-temperature cycle characteristic) and self-discharging is small even when the battery is placed in a fully charged state for a long period of time under a high temperature environment (a high-temperature storage characteristic).

As a means for improving the high-temperature characteristic, and the battery characteristic (a cycle characteristic) wherein charging and discharging are repeated, optimization of various battery components including active materials of positive electrodes and negative electrodes has been studied. A non-aqueous electrolyte solution-related technology is not an exception, and it has been proposed that deterioration due to decomposition of an electrolyte solution on the surface of an active positive electrode or an active negative electrode is suppressed by various additives. For example, Patent Document 1 proposes that battery characteristics are improved by the addition of a vinylene carbonate to an electrolyte solution. However, there was a problem in that battery characteristics at high temperatures are improved, but the internal resistance is significantly increased to lower the low-temperature characteristic. Addition of a silicon compound to an electrolyte solution has been also studied. Alternatively, examination has been made on addition of a silicon compound to an electrolyte solution, for example, as shown in Patent Documents 2 to 6, which propose addition of a silicon compound such as a silicone compound or a fluorosilane compound, to a non-aqueous electrolyte solution for the purpose of improving a cycle characteristic of the non-aqueous electrolyte battery and for inhibiting internal resistance elevation so as to improve a high-temperature storage characteristic and a low-temperature characteristic of the non-aqueous electrolyte battery. In addition, Patent Document 7 proposes addition of a fluorosilane compound or a difluorophosphoric acid compound in order to improve a low-temperature characteristic of the non-aqueous electrolyte battery. Furthermore, examination has been conducted on the addition of a salt containing a phosphoryl group or a sulfonyl group to an electrolyte solution. For example, there have been proposed a method (Patent Document 8) for improving a high-temperature cycle characteristic or a high-temperature storage characteristic by combining a specific sulfonimide salt or phosphoryl imide salt with an oxalato complex; and a method (Patent Document 9) for improving a cycle characteristic or an output characteristic by combining a specific fluorophosphate with a sulfonimide salt.

PRIOR ART DOCUMENTS

Patent Documents

Patent Document 1: JP Patent Publication (Kokai) No. 2000-123867 A
Patent Document 2: JP Patent Publication (Kokai) No. 8-078053 A
Patent Document 3: JP Patent Early-Publication (Kokai) No. 2002-033127 A
Patent Document 4: JP Patent Early-Publication (Kokai) No. 2004-039510 A
Patent Document 5: JP Patent Early-Publication (Kokai) No. 2004-087459 A
Patent Document 6: JP Patent Early-Publication (Kokai) No. 2008-181831 A
Patent Document 7: JP Patent Early-Publication (Kokai) No. 2007-149656 A
Patent Document 8: JP Patent Early-Publication (Kokai) No. 2013-051122 A
Patent Document 9: JP Patent Early-Publication (Kokai) No. 2013-030465 A
Patent Document 10: JP Patent Early-Publication (Kokai) No. 10-139784 A
Patent Document 11: JP Patent Early-Publication (Kokai) No. 2008-222484 A

Non-Patent Documents

Non-patent Document 1: Tetrahedron, 42(11), 2821-2829 (1986)
Non-patent Document 2: Journal of the American Chemical Society, 72, 4956-4958, (1950)
Non-patent Document 3: Faraday Discussion, 145, 281-299, (2010)

SUMMARY OF THE INVENTION

Problem to be Solved by the Invention

There is still a room for the batteries disclosed in the Prior Art Documents in order to improve the low-temperature output characteristic, high-temperature cycle characteristic, and high-temperature storage characteristic. In particular, there is a problem for the batteries that at a low temperature, since the internal resistance of the batteries is increased, discharge voltage is largely decreased and accordingly it is not possible to obtain sufficient discharge voltage. Further, there is a problem in that, when a silane compound having an Si—F bond or an Si—O bond is used, the internal resistance of the batteries is extremely high and accordingly the output characteristic is greatly reduced. The present invention provides an electrolyte solution for a non-aqueous electrolyte battery capable of exerting a high average discharge voltage and an excellent low-temperature output characteristic at −30° C. or lower and an excellent cycle characteristic and an excellent storage characteristic at high temperatures of 50° C. or higher, as well as a non-aqueous electrolyte battery containing the same.

Means for Solving the Problems

The present inventors have made intensive studies in order to resolve the above mentioned problems, and as a result, have discovered that a non-aqueous electrolyte battery can exert an excellent low-temperature characteristic, a high-temperature cycle characteristic, and a high-temperature storage characteristic, when a non-aqueous electrolyte solution for a non-aqueous electrolyte battery containing a non-aqueous solvent and a solute contains (1) a specific silane compound and (2) at least one compound selected from the group consisting of a fluorine-containing compound having a specific structure (a fluorophosphate having a specific structure, an imide salt having a specific fluorophosphoryl structure and/or a specific fluorosulfonyl structure). The present invention has been completed based on this finding.

Specifically, the present invention provides an electrolyte solution for a non-aqueous electrolyte battery (which may be sometimes hereinafter also referred to simply as "non-aqueous electrolyte solution" or "electrolyte solution"), including at least a non-aqueous solvent, a solute, at least one silane compound represented by the following general formula (1) as a first compound, and at least one compound selected from the group consisting of fluorine-containing compounds represented by the following general formulae (2) to (9) as a second compound.

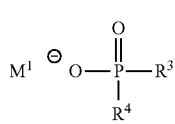

(1)

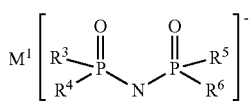

(2)

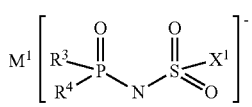

(3)

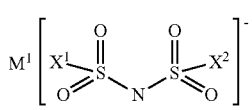

(4)

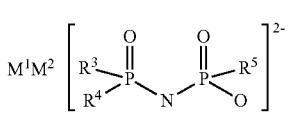

(5)

(6)

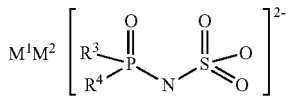

(7)

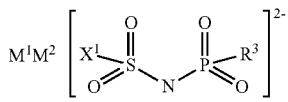

(8)

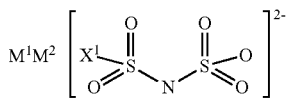

(9)

In general formula (1),
$R^1$ each independently represents a group having a carbon-carbon unsaturated bond,
$R^2$ each independently represents a linear or branched $C_{1\text{-}10}$ alkyl group, which may optionally contain a fluorine atom and/or an oxygen atom, and
a is 2 to 4.
In general formulae (2) to (4) and (6) to (8),
$R^3$ to $R^6$ each independently represent a fluorine atom or an organic group selected from a linear or branched $C_{1\text{-}10}$ alkoxy group, a $C_{2\text{-}10}$ alkenyloxy group, a $C_{2\text{-}10}$ alkynyloxy group, a $C_{3\text{-}10}$ cycloalkoxy group, a $C_{3\text{-}10}$ cycloalkenyloxy group, and a $C_{6\text{-}10}$ aryloxy group, wherein a fluorine atom, an oxygen atom, or an unsaturated bond may optionally be present in the organic group as well.
In general formulae (4), (5), (8), and (9),
$X^1$ and $X^2$ each independently represent a fluorine atom or an organic group selected from a linear or branched $C_{1\text{-}10}$ alkyl group, a $C_{2\text{-}10}$ alkenyl group, a $C_{2\text{-}10}$ alkynyl group, a $C_{3\text{-}10}$ cycloalkyl group, a $C_{3\text{-}10}$ cycloalkenyl group, a $C_{6\text{-}10}$ aryl group, a linear or branched $C_{1\text{-}10}$ alkoxy group, a $C_{2\text{-}10}$ alkenyloxy group, a $C_{2\text{-}10}$ alkynyloxy group, a $C_{3\text{-}10}$ cycloalkoxy group, a $C_{3\text{-}10}$ cycloalkenyloxy group, and a $C_{6\text{-}10}$ aryloxy group, wherein a fluorine atom, an oxygen atom, or an unsaturated bond may optionally be present in the organic group as well.
The general formulae (2) to (9) have at least one P—F bond and/or at least one S—F bond.
$M^1$ and $M^2$ each independently represent a proton, a metal cation or an onium cation.
It is important that the electrolyte solution for a non-aqueous electrolyte battery of the present invention comprises the first compound and the second compound in combination. The reason is that, only when including these two compounds in combination, the electrolyte solution used in a non-aqueous electrolyte battery can exert a high average discharge voltage and excellent low-temperature output characteristics at −30° C. or lower and an excellent cycle characteristics and excellent storage characteristics at high temperatures of 50° C. or higher.

The amount of the first compound to be added preferably ranges from 0.001 to 10.0% by mass relative to the total amount of the electrolyte solution for a non-aqueous electrolyte battery.

The amount of the second compound to be added preferably ranges from 0.001 to 10.0% by mass relative to the total amount of the electrolyte solution for a non-aqueous electrolyte battery.

The group represented by $R^1$ in the general formula (1) preferably each independently represents a group selected from the group consisting of a vinyl group, an allyl group, a 1-propenyl group, a 2-propenyl group, an ethynyl group, and a 2-propynyl group.

The group represented by $R^2$ in the general formula (1) preferably each independently represents a group selected from the group consisting of a methyl group, an ethyl group, a propyl group, a 2,2,2-trifluoroethyl group, a 2,2,3,3-tetrafluoropropyl group, a 1,1,1-trifluoroisopropyl group, and a 1,1,1,3,3,3-hexafluoroisopropyl group.

$R^3$ to $R^6$ in the general formulae (2) to (4) and (6) to (8) preferably represent a fluorine atom or an organic group selected from the group consisting of a fluorine-containing linear or branched $C_{1-10}$ alkoxy group, a $C_{2-10}$ alkenyloxy group, and a $C_{2-10}$ alkynyloxy group.

It is more preferable that the alkoxy group is selected from the group consisting of a 2,2,2-trifluoroethoxy group, a 2,2,3,3-tetrafluoropropoxy group, a 1,1,1-trifluoroisopropoxy group, and a 1,1,1,3,3,3-hexafluoroisopropoxy group, the alkenyloxy group is selected from the group consisting of a 1-propenyloxy group, a 2-propenyloxy group, and a 3-butenyloxy group, and the alkynyloxy group is selected from the group consisting of a 2-propynyloxy group and a 1,1-dimethyl-2-propynyloxy group.

$X^1$ and $X^2$ in the general formulae (4), (5), (8), and (9) is preferably a fluorine atom or an organic group selected from the group consisting of a linear or branched $C_{1-10}$ alkoxy group, a $C_{2-10}$ alkenyloxy group and a $C_{2-10}$ alkynyloxy group.

It is preferable that the alkoxy group is selected from the group consisting of a methoxy group, an ethoxy group, and a propoxy group, the alkenyloxy group is selected from the group consisting of a 1-propenyloxy group, a 2-propenyloxy group, and a 3-butenyloxy group, and the alkynyloxy group is selected from the group consisting of a 2-propynyloxy group and a 1,1-dimethyl-2-propynyloxy group.

$M^1$ and $M^2$ in the general formulae (2) to (9) preferably represent at least one cation selected from the group consisting of a lithium ion, a sodium ion, a potassium ion, a tetraalkylammonium ion, and a tetraalkylphosphonium ion.

The solute is preferably at least one solute selected from the group consisting of lithium hexafluorophosphate ($LiPF_6$), lithium tetrafluoroborate ($LiBF_4$), lithium bis(trifluoromethanesulfonyl)imide ($LiN(CF_3SO_2)_2$), lithium bis(fluorosulfonyl)imide ($LiN(FSO_2)_2$), lithium bis(difluorophosphoryl)imide ($LiN(POF_2)_2$), sodium hexafluorophosphate ($NaPF_6$), sodiumtetrafluoroborate ($NaBF_4$), sodium bis(trifluoromethanesulfonyl)imide ($NaN(CF_3SO_2)_2$), sodium bis(fluorosulfonyl)imide ($NaN(FSO_2)_2$), and sodium bis(difluorophosphoryl)imide ($NaN(POF_2)_2$).

The non-aqueous solvent is preferably at least one non-aqueous solvent selected from the group consisting of a cyclic carbonate, a linear carbonate, a cyclic ester, a linear ester, a cyclic ether, a linear ether, a sulfone compound, a sulfoxide compound, and an ionic liquid.

The present invention provides a non-aqueous electrolyte battery (which may be sometimes hereinafter also referred to simply as "non-aqueous battery" or "battery"), comprising at least a positive electrode, a negative electrode, a separator, and the electrolyte solution for a non-aqueous electrolyte battery as stated above.

Effects Of The Invention

The present invention can provide an electrolyte solution for a non-aqueous electrolyte battery capable of exerting a high average discharge voltage and excellent low-temperature output characteristics at −30° C. or lower and an excellent cycle characteristics and excellent storage characteristics at high temperatures of 50° C. or higher when used for a non-aqueous electrolyte battery, as well as a non-aqueous electrolyte battery containing the same.

MODES FOR CARRYING OUT THE INVENTION

The present invention will be described in detail. However, the explanations for the constituent features described below are merely examples of the embodiments of the present invention, and the scope of the present invention is not limited to these specific embodiments. The present invention may be variously modified and implemented within the whole disclosure of the present application.

The electrolyte solution for a non-aqueous electrolyte battery of the present invention is an electrolyte solution for a non-aqueous electrolyte battery, comprising at least a non-aqueous solvent, a solute, at least one silane compound represented by the above general formula (1) as a first compound, and at least one compound selected from the group consisting of fluorine-containing compounds represented by the above general formulae (2) to (9) as a second compound.

The first compound decomposes on a positive electrode and/or a negative electrode so as to form a stable film, which suppresses deterioration of the battery. In the case wherein the first compound is not used in combination with the second compound but the first compound is only used, there would be generated a problem in that the film formed on the electrode serves as a great resistance to the movement of lithium ions during charge and discharge, whereby the resultant non-aqueous electrolyte battery has markedly decreased low-temperature characteristics. In addition, the high-temperature cycle characteristic and a high-temperature storage characteristic at high temperatures of 50° C. or higher are insufficient.

Similarly, the second compound partially decomposes on a positive electrode and/or a negative electrode, so as to form a highly ionically-conductive film on the surfaces of the positive electrode and the negative electrode. This film prevents the non-aqueous solvent and the solute from directly contacting an electrode active material, thereby preventing decomposition of the non-aqueous solvent and the solute, suppressing deterioration of battery performance. In the case wherein the second compound is not used together with the first compound and the second compound is singly used, the number of the film forming components is small, whereby the resultant non-aqueous electrolyte battery has an insufficient high-temperature cycle characteristic and an insufficient high-temperature storage characteristic at high temperatures of 50° C. or higher as well as an insufficient low-temperature characteristic.

By using the first compound and the second compound together in the electrolyte solution for a non-aqueous electrolyte battery of the present invention, when compared to the case wherein the first compound is singly used, the high-temperature cycle characteristic and high-temperature storage characteristic at high temperatures of 50° C. or higher as well as a low-temperature characteristic are improved, whereby the object of the present invention is successfully achieved. The detailed mechanism of this phenomenon is not clear, but it is assumed as follows: when the first and second compounds are present together, both of the first compound and the second compound actively decompose on the positive electrode and negative electrode, so that the resultant film has a higher ionic conductance and durability than the single use of either of the first and second compounds. It is considered that this indicates that the decomposition of the solvent and the solute at high temperatures is suppressed and resistance elevation at low temperatures is also suppressed. In particular, it is assumed that a more amount of fluorophosphoryl structure and/or fluorosulfonyl structure is contained in the resultant film and accordingly, there is caused a deviation in charge distribution within the film, which imparts the film with a high lithium conductivity, i.e. the film having a low resistance (this means that the film has a good output characteristic). It is also assumed that the more the amount of unsaturated bond containing moieties is contained in the first compound and the second compound, the more likely the first compound and the second compound are to decompose on the positive electrode and the negative electrode, the higher the durability of the resultant film is, and the more excellent the effects described above are. It is also assumed that when a moiety having a higher electron withdrawing (fluorine atoms and fluorine containing alkoxy groups, for example) is contained in the second compound, the deviation in charge distribution becomes larger, whereby a lower resistant film (the film having a better output characteristic) is formed.

For the reasons as stated above, it is assumed that the use of the first compound and the second compound together improves an average discharge voltage (output characteristic) at temperatures of −30° C. or lower and a cycle characteristic and a storage characteristic at high temperatures of 50° C. or higher, as compared with the single use of either of the first and second compounds.

The electrolyte solution for a non-aqueous electrolyte battery of the present invention comprises the first compound, the second compound, a non-aqueous organic solvent, and the solute. If necessary, the electrolyte solution for a non-aqueous electrolyte battery of the present invention may also comprise another additive which is generally known in the art. In the following, the constituent elements of the electrolyte solution for a non-aqueous electrolyte battery of the present invention will be described in detail. First Compound Examples of the group represented as $R^1$ in the above general formula (1) having a carbon-carbon unsaturated bond include $C_{2-8}$ alkenyl groups such as a vinyl group, an allyl group, a 1-propenyl group, a 2-propenyl group, an isopropenyl group, a 2-butenyl group, and a 1,3-butadienyl group, alkenyloxy groups derived from these $C_{2-8}$ alkenyl groups, $C_{2-8}$ alkynyl groups such as an ethynyl group, a 2-propynyl group, and a 1,1-dimethyl-2-propynyl group, alkynyloxy groups derived from these $C_{2-8}$ alkynyl groups, $C_{6-12}$ aryl groups such as a phenyl group, a tolyl group, and a xylyl group, and aryloxy groups derived from these $C_{6-12}$ aryl groups. The group represented as $R^1$ may contain a fluorine atom and/or an oxygen atom. Among them, those groups which contain 6 or less carbons and have a carbon-carbon unsaturated bond are preferable. In the case wherein the number of the carbons is greater than 6, the resistance after a film is formed on the electrode tends to be relatively high. More specifically, the group selected from the group consisting of a vinyl group, an allyl group, a 1-propenyl group, a 2-propenyl group, an ethynyl group and a 2-propynyl group is preferable.

The number of groups having a carbon-carbon unsaturated bond is required to be from 2 to 4 in order to form a film on an electrode, eventually in order to attain the object of the present invention, and is preferably from 3 to 4 in order to form a strong film.

Examples of the alkyl group represented as $R^2$ in the above general formula (1) include $C_{1-12}$ alkyl groups such as a methyl group, an ethyl group, a propyl group, an isopropyl group, an n-butyl group, a sec-butyl group, an isobutyl group, a tert-butyl group and a pentyl group. The alkyl group represented as $R^2$ may contain a fluorine atom and/or an oxygen atom (in the case wherein an oxygen atom is contained, the alkyl group represented as $R^2$ means a structure other than an alkoxy group; more specifically, the oxygen atom is not bonded to the silicon atom in general formula (1)). Among these groups, those groups selected from the group consisting of a methyl group, an ethyl group, a propyl group, a 2,2,2-trifluoroethyl group, a 2,2,3,3-tetrafluoropropyl group, a 1,1,1-trifluoroisopropyl group, and a 1,1,1,3,3,3-hexafluoroisopropyl group are particularly preferable, in order to provide a non-aqueous electrolyte battery having a more improved high-temperature cycle characteristic and high-temperature storage characteristic, without increasing the internal resistance of the battery.

The lower limit of the amount of the first compound to be added is preferably 0.001% by mass or more, more preferably 0.01% by mass or more, further more preferably 0.1% by mass or more, and the upper limit of the amount of the first compound to be added is preferably 10.0% by mass or less, more preferably 5.0% by mass or less, further more preferably 2.0% by mass or less relative to the total amount of the electrolyte solution for a non-aqueous electrolyte battery. The amount of the first compound to be added that is lower than 0.001% by mass may make it difficult to obtain an effect of sufficiently improving a high-temperature storage characteristic of the resultant non-aqueous electrolyte battery. On the other hand, the amount of the first compound to be added of higher than 10.0% by mass may greatly increase the internal resistance of the battery, which would cause a problem in that the low-temperature output characteristic is impaired. One kind of the first compound may be singly used, or a plurality of kinds thereof may be used. The term "the total amount of the electrolyte solution for a non-aqueous electrolyte battery" refers to the sum of the amounts of all the non-aqueous solvent, the solute, the first compound and the second compound.

Specific examples of the silane compound represented by the above general formula (1) include the following compounds No.1 to No.13. However, the silane compound used in the present invention is not limited to these compounds.

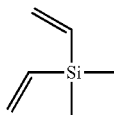

Compound No. 1

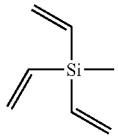

Compound No. 2

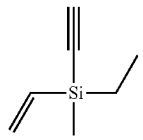

Compound No. 3

-continued

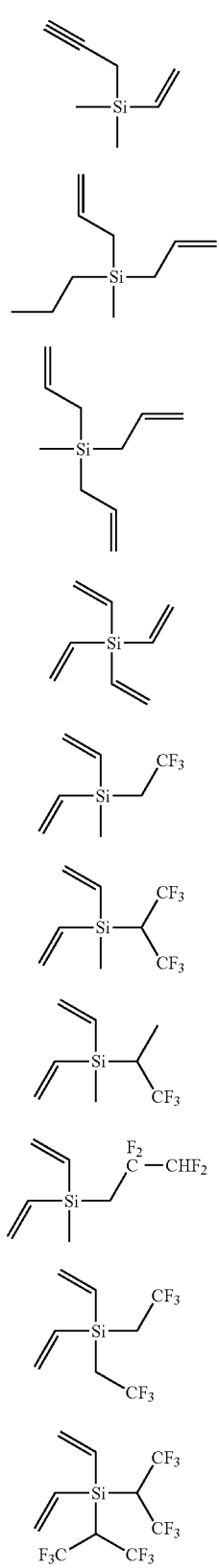

Compound No. 4

Compound No. 5

Compound No. 6

Compound No. 7

Compound No. 8

Compound No. 9

Compound No. 10

Compound No. 11

Compound No. 12

Compound No. 13

The silane compound represented by the above general formula (1) may be produced, as described in Patent Document 10 and Non-patent Document 1, for example, by reacting a silicon compound containing a silanol group or a hydrolyzable group with an organic metal reagent having a carbon-carbon unsaturated bond, so as to replace the silanol group or the hydrolyzable group in the silicon compound by the group having a carbon-carbon unsaturated bond, thus producing the present silicon compound having a carbon-carbon unsaturated bond.

Second Compound

It is important for achieving the object of the present invention that the above general formulae (2) to (9) have at least one of a P—F bond and/or S—F bond. When no P—F bond or S—F bond is contained, a low-temperature characteristic cannot be improved. The more the number of P—F bonds and S—F bonds is, the more excellent low-temperature characteristic is obtained, and is preferable.

Examples of the cation represented as $M^1$ and $M^2$ in the above general formulae (2) to (9) include a proton, a metal cation, and an onium cation. Any type of the cations may be used with no restrictions, so long as they do not deteriorate the performance of the electrolyte solution for a non-aqueous electrolyte battery of the present invention and the non-aqueous electrolyte battery, and any cations may be selected from among the cations as stated above without any restrictions. Specific examples thereof include cations of metals such as lithium, sodium, potassium, rubidium, cesium, magnesium, calcium, barium, silver, copper and iron, and cations of oniums such as tetraalkylammonium, tetraalkylphosphonium and imidazolium derivatives. From the viewpoint of improving ionic conductance within the non-aqueous electrolyte battery, a lithium ion, a sodium ion, a potassium ion, a tetramethylammonium ion, a tetraethylammonium ion, a tetrabutylphosphonium ion, and the like are particularly preferable.

In the above general formulae (2) to (4) and (6) to (8), the alkoxy group represented by $R^3$ to $R^6$ includes $C_{1-10}$ alkoxy groups and fluorine-containing alkoxy groups, such as a methoxy group, an ethoxy group, a propoxy group, an isopropoxy group, a butoxy group, a secondary butoxy group, a tertiary butoxy group, a pentyloxy group, a trifluoromethoxy group, a 2,2-difluoroethoxy group, a 2,2,2-trifluoroethoxy group, a 2,2,3,3-tetrafluoropropoxy group, a 1,1,1-trifluoroisopropoxy group, and a 1,1,1,3,3,3-hexafluoroisopropoxy group; the alkenyloxy group represented by $R^3$ to $R^6$ includes $C_{2-10}$ alkenyloxy groups and fluorine-containing alkenyloxy groups, such as a vinyloxy group, a 1-propenyloxy group, a 2-propenyloxy group, anisopropenyloxy group, a 2-butenyloxy group, a 3-butenyloxy group and a 1,3-butadienyloxy group; the alkynyloxy group represented by $R^3$ to $R^6$ includes $C_{2-10}$ alkynyloxy groups and fluorine-containing alkynyloxy groups, such as an ethynyloxy group, a 2-propynyloxy group and a 1,1-dimethyl-2-propynyloxy group; the cycloalkoxy group represented by $R^3$ to $R^6$ includes $C_{3-10}$ cycloalkoxy groups and fluorine-containing cycloalkoxy groups, such as a cyclopentyloxy group and a cyclohexyloxy group; the cycloalkenyloxy group represented by $R^3$ to $R^6$ includes $C_{3-10}$ cycloalkenyloxy groups and fluorine-containing cycloalkenyloxy groups, such as a cyclopentenyloxy group and a cyclohexenyloxy group; and the aryloxy group represented by $R^3$ to $R^6$ includes $C_{6-10}$ aryloxy groups and fluorine-containing aryloxy groups, such as a phenyloxy group, a tolyloxy group and a xylyloxy group.

$R^3$ to $R^6$ in the above general formulae (2) to (4) and (6) to (8) are preferably fluorine atoms or alkoxy groups containing a fluorine atom, because the strong electron-withdrawing property thereof improves ion dissociation degree, thereby increasing ionic conductance in a solution and a composition. Further, $R^3$ to $R^6$ in the above general formulae (2) to (4) and (6) to (8) are more preferably fluorine atoms, because the smaller anion size improves mobility, so as to significantly increase the degree of ionic conductance in a solution or a composition. For this reason, it is assumed that the greater the number of P—F bonds in the above general formulae (2) to (9) is, the greater the low-temperature characteristic is improved. Furthermore, the above $R^3$ to $R^6$ are preferably organic groups selected from the group consisting of an alkenyloxy group and an alkynyloxy group. Unlike the above alkenyloxy group and alkynyloxy group, a hydrocarbon group with no intervening oxygen atom is not preferred because of its weak electron-withdrawing property which causes a decrease in ion dissociation degree and a decrease in ionic conductance in a solution or a composition. As in the case of the alkenyloxy group and the alkynyloxy group, a group having an unsaturated bond is preferable because decomposition on the positive electrode and the negative electrode proceeds actively and the resultant film is higher in durability. Furthermore, the high number of carbons tends to result in an increased anion size and decreased ionic conductance in a solution or a composition, and accordingly, the number of carbons of the above $R^3$ to $R^6$ is preferably 6 or less. When the number of carbons is 6 or less, the resultant ionic conductance tends to be relatively high and accordingly is preferable. The organic group is particularly preferably a group selected from the group consisting of a 1-propenyloxy group, a 2-propenyloxy group, a 3-butenyloxy group, a 2-propynyloxy group and a 1,1-dimethyl-2-propynyloxy group, because of their relatively small anion sizes.

In the above general formulae (4), (5), (8), and (9), the alkyl group represented by $X^1$ and $X^2$ includes $C_{1-10}$ alkyl groups and fluorine-containing alkyl groups, such as a methyl group, an ethyl group, a propyl group, an isopropyl group, a butyl group, a secondary butyl group, a tertiary butyl group, a pentyl group, a trifluoromethyl group, a 2,2-difluoroethyl group, a 2,2,2-trifluoroethyl group, a 2,2,3,3-tetrafluoropropyl group and a 1,1,1,3,3,3-hexafluoroisopropyl group; the alkenyl group represented by $X^1$ and $X^2$ includes $C_{2-10}$ alkenyl groups and fluorine-containing alkenyl groups, such as a vinyl group, a 1-propenyl group, a 2-propenyl group, an isopropenyl group, a 2-butenyl group, a 3-butenyl group and a 1,3-butadienyl group; the alkynyl group represented by $X^1$ and $X^2$ includes $C_{2-10}$ alkynyl groups and fluorine-containing alkynyl groups, such as an ethynyl group, a 2-propynyl group and a 1, 1-dimethyl-2-propynyl group; the cycloalkyl group represented by $X^1$ and $X^2$ includes $C_{3-10}$ cycloalkyl. groups and fluorine-containing cycloalkyl groups, such as a cyclopentyl group and a cyclohexyl group; the cycloalkenyl group represented by $X^1$ and $X^2$ includes $C_{3-10}$ cycloalkenyl groups and fluorine-containing cycloalkenyl groups, such as a cyclopentenyl group and a cyclohexenyl group; the aryl group represented by $X^1$ and $X^2$ includes $C_{6-10}$ aryl groups and fluorine-containing aryl groups, such as a phenyl group, a tolyl group and a xylyl group; the alkoxy group represented by $X^1$ and $X^2$ includes $C_{1-10}$ alkoxy groups and fluorine-containing alkoxy groups, such as a methoxy group, an ethoxy group, a propoxy group, an isopropoxy group, a butoxy group, a secondary butoxy group, a tertiary butoxy group, a pentyloxy group, a trifluoromethoxy group, a 2,2-difluoroethoxy group, a 2,2,2-trifluoroethoxy group, a 2,2,3,3-tetrafluoropropoxy group and a 1,1,1,3,3,3-hexafluoroisopropoxy group; the alkenyloxy group represented by $X^1$ and $X^2$ includes $C_{2-10}$ alkenyloxy groups and fluorine-containing alkenyloxy groups, such as a vinyloxy group, a 1-propenyloxy group, a 2-propenyloxy group, an isopropenyloxy group, a 2-butenyloxy group, a 3-butenyloxy group and a 1,3-butadienyloxy group; the alkynyloxy group represented by $X^1$ and $X^2$ includes $C_{2-10}$ alkynyloxy groups and fluorine-containing alkynyloxy groups, such as an ethynyloxy group, a 2-propynyloxy group and a 1,1-dimethyl-2-propynyloxy group; the cycloalkoxy group represented by $X^1$ and $X^2$ includes $C_{3-10}$ cycloalkoxy groups and fluorine-containing cycloalkoxy groups, such as a cyclopentyloxy group and a cyclohexyloxy group; the cycloalkenyloxy group represented by $X^1$ and $X^2$ includes $C_{3-10}$ cycloalkenyloxy groups and fluorine-containing cycloalkenyloxy groups, such as a cyclo pentenyloxy group and a cyclohexenyloxy group; and the aryloxy group represented by $X^1$ and $X^2$ includes $C_{6-10}$ aryloxy groups and fluorine-containing aryloxy groups, such as a phenyloxy group, a tolyloxy group and a xylyloxy group.

$X^1$ and $X^2$ in the above general formulae (4), (5), (8), and (9) are preferably fluorine atoms, because the strong electron-withdrawing property of fluorine atom improves ion dissociation degree and its lower anion size improves mobility, so as to significantly increase the degree of ionic conductance in a solution or a composition. Furthermore, the above $X^1$ and $X^2$ are preferably organic groups selected from the group consisting of an alkoxy group, an alkenyloxy group and an alkynyloxy group. Unlike the above alkoxy group, alkenyloxy group, and alkynyloxy group, a hydrocarbon group with no intervening oxygen atom is not preferred because of its weak electron-withdrawing property, which causes a decrease in ion dissociation degree and a decrease in ionic conductance in a solution or a composition. Furthermore, the higher number of carbons tends to result in an increased anion size and decreased ionic conductance in a solution or a composition. Hence, the number of carbons of the above X is preferably 6 or less. It is preferable that when the number of carbons is 6 or less, the resultant ionic conductance tends to be relatively high. The organic group is particularly preferably when it is selected from the group consisting of a methoxy group, an ethoxy group, a propoxy group, a 1-propenyloxy group, a 2-propenyloxy group, a 3-butenyloxy group, a 2-propynyloxy group and a 1,1-dimethyl-2-propynyloxy group, because of their relatively small anion sizes.

In the case wherein the compound has the structure as represented by any of the above general formula (2), (6), (7) and (8) wherein all of $R^3$ to $R^5$ and $X^1$ are hydrocarbon groups with an intervening oxygen atom (an alkoxy group, an alkenyloxy group, an alkynyloxy group, a cycloalkoxy group, a cycloalkenyloxy group and an aryloxy group), more specifically the compound containing no a P—F bond or an S—F bond, the solubility of the compound in the non-aqueous electrolyte solution is very low (lower than 0.001% by mass, for example) and therefore it is difficult to achieve the object of the present invention even when such a compound is added to the non-aqueous electrolyte solution.

The lower limit of the amount of the second compound to be added is preferably 0.001% by mass or more, more preferably 0.01% by mass or more, further more preferably 0.1% by mass or more, and the upper limit of the amount of the second compound to be added is preferably 10.0% by mass or less, more preferably 5.0% by mass or less, further more preferably 2.0% by mass or less, relative to the total amount of the electrolyte solution for a non-aqueous electrolyte battery. When the amount of the second compound to be added is lower than 0.001% by mass, it may be difficult to sufficiently improve an output characteristic of the resultant non-aqueous electrolyte battery at low temperatures. On the other hand, when the amount of the second compound to be added is higher than 10.0% by mass, the improving effect cannot be obtained even by the addition of more than 10.0% by mass, and such addition is not only useless, but also tends to increase the viscosity of the electrolyte solution and decrease the ionic conductance, which easily increases the resistance and deteriorates the battery performance, and thus is not preferred. One type of the second compound may be added alone, or plural types of the second compounds may be added in combination.

Specific examples of the phosphate anion represented by the above general formula (2) include the following compound No.14. However, the phosphate used in the present invention is not limited to such a compound.

Compound No. 14

Specific examples of the imide salt anion represented by the above general formulae (3) to (9) include the following compounds No.15 to No.50. However, the imide salt used in the present invention is not limited to these compounds.

Compound No. 15

Compound No. 16

Compound No. 17

Compound No. 18

Compound No. 19

Compound No. 20

Compound No. 21

Compound No. 22

Compound No. 23

Compound No. 24

Compound No. 25

Compound No. 26

Compound No. 27

Compound No. 28

Compound No. 29

Compound No. 30

Compound No. 31

Compound No. 32

Compound No. 33

Compound No. 34

Compound No. 35

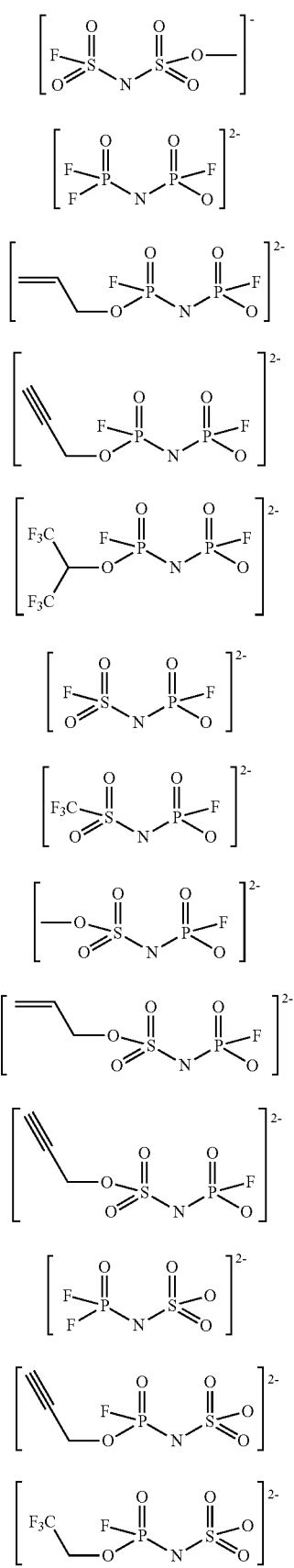

Compound No. 36

Compound No. 37

Compound No. 38

Compound No. 39

Compound No. 40

Compound No. 41

Compound No. 42

Compound No. 43

Compound No. 44

Compound No. 45

Compound No. 46

Compound No. 47

Compound No. 48

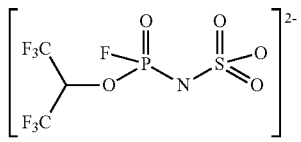

Compound No. 49

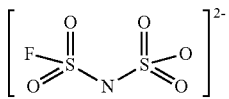

Compound No. 50

A salt having the phosphate anion represented by the above general formula (2) may be produced, as described in Patent Document 11, Non-patent Document 2, and Non-patent Document 3, for example, by reacting a halide other than a fluoride, with $LiPF_6$ and water in a non-aqueous solvent, or by reacting a pyrophosphoric acid ester containing an corresponding alkoxy group with hydrogen fluoride.

A salt having the imide anion represented by the above general formula (3) may be produced by any of various methods with no limitation. For example, the salt may be produced by reacting a corresponding phosphoryl chloride $(P(=O)R^3R^4Cl)$ with a phosphoramide $(H_2NP(=O)R^5R^6)$ in the presence of an organic base or an inorganic base.

A salt having the imide anion represented by the above general formula (4) may be produced by any of various methods with no limitation. For example, the salt may be produced by reacting a corresponding phosphoryl chloride $(P(=O)R^3R^4Cl)$ with a sulfonamide $(H_2NSO_2X^1)$ in the presence of an organic base or an inorganic base.

A salt having the imide anion represented by the above general formula (5) may be produced by any of various methods with no limitation. For example, the salt may be produced by reacting a corresponding sulfonyl chloride $(X^1SO_2Cl)$ with a corresponding sulfonamide $(H_2NSO_2X^2)$ in the presence of an organic base or an inorganic base.

A salt having the imide anion represented by the above general formula (6) may be produced by any of various methods with no limitation. For example, the salt may be produced by reacting a corresponding phosphoryl chloride $(P(=O)R^3R^4Cl)$ with a corresponding phosphoramide $(H_2NP(=O)R^5O^-)$ in the presence of an organic base or an inorganic base.

A salt having the imide anion represented by the above general formula (7) may be produced by any of various methods with no limitation. For example, the salt may be produced by reacting a corresponding phosphoryl chloride $(P(=O)R^3R^4Cl)$ with sulfamic acid $(H_2NSO_3^-)$ in the presence of an organic base or an inorganic base.

A salt having the imide anion represented by the above general formula (8) may be produced by any of various methods with no limitation. For example, the salt may be produced by reacting a corresponding sulfonyl chloride $(X^1SO_2Cl)$ with a corresponding phosphoramide $(H_2NP(=O)R^3O^-)$ in the presence of an organic base or an inorganic base.

A salt having the imide anion represented by the above general formula (9) may be produced by any of various methods with no limitation. For example, the salt may be produced by reacting a corresponding sulfonyl chloride $(X^1SO_2Cl)$ with a corresponding sulfamic acid $(H_2NSO_3^-)$ in the presence of an organic base or an inorganic base.

In these methods of producing the salts represented by general formulae (2) to (9) as stated above, cation exchange may be performed if appropriate.

Non-aqueous Solvent

Kinds of non-aqueous solvent to be used for the electrolyte solution for a non-aqueous electrolyte battery of the present invention are not particularly limited, and any kinds of non-aqueous solvents can be used. Specific examples thereof include cyclic carbonates such as propylene carbonate, ethylene carbonate, butylene carbonate and fluoroethylene carbonate; linear carbonates such as diethyl carbonate, dimethyl carbonate and ethyl methyl carbonate; cyclic esters such as γ-butyrolactone and γ-valerolactone; linear esters such as methyl acetate and methyl propionate; cyclic ethers such as tetrahydrofuran, 2-methyltetrahydrofuran and dioxane; linear ethers such as dimethoxyethane and diethylether; and sulfone compounds or sulfoxide compounds such as dimethyl sulfoxide and sulfolane. An ionic liquid and the like, whose category is different from that of the above non-aqueous solvents may be also used. Furthermore, one type of non-aqueous solvent may be used in the present invention or two or more types thereof with differing mixing ratios and in any combination may be used depending on applications. Of these examples, in view of electrochemical stability against its oxidation-reduction and chemical stability relating to heat or reaction with the above solute, propylene carbonate, ethylene carbonate, fluoroethylene carbonate, diethyl carbonate, dimethyl carbonate and ethyl methyl carbonate are particularly preferred.

Solute

Any kinds of the solutes may be used for the electrolyte solution for a non-aqueous electrolyte battery of the present invention and are not particularly limited, and any kinds of electrolyte salts can be used. Specific examples thereof include: in the case of a lithium battery and a lithium ion battery, electrolyte salts represented by $LiPF_6$, $LiBF_4$, $LiClO_4$, $LiAsF_6$, $LiSbF_6$, $LiCF_3SO_3$, $LiN(CF_3SO_2)_2$, $LiN(FSO_2)_2$, $LiN(C_2F_5SO_2)_2$, $LiN(CF_3SO_2)(C_4F_9SO_2)$ $LiC(CF_3SO_2)_3$, $LiPF_3(C_3F_7)_3$, $LiB(CF_3)_4$, $LiBF_3(C_2F_5)$, and $LiN(POF_2)_2$; and in the case of a sodium ion battery, electrolyte salts represented by $NaPF_6$, $NaBF_4$, $NaCF_3SO_3$, $NaN(CF_3SO_2)_2$, $NaN(FSO_2)_2$, and $NaN(POF_2)_2$. One kind of the solute may be used independently, and two or more types thereof may be mixed at any ratio and in any combination, depending on applications. Of these examples, in view of energy density, output characteristic, life and the like for a battery, $LiPF_6$, $LiBF_4$, $LiN(CF_3SO_2)_2$, $LiN(FSO_2)_2$, $LiN(C_2F_5SO_2)_2$, $LiN(POF_2)_2$, $NaPF_6$, $NaBF_4$, $NaN(CF_3SO_2)_2$, $NaN(FSO_2)_2$, and $NaN(POF_2)_2$ are preferred.

The concentration of the solute is not particularly limited. The lower limit of the concentration is preferably 0.5 mol/L or more, more preferably 0.7 mol/L or more, further more preferably 0.9 mol/L or more, and the upper limit of the concentration is preferably 2.5 mol/L or less, more preferably 2.0 mol/L or less, further more preferably 1.5 mol/L or less. When the concentration is lower than 0.5 mol/L, there may be caused a decrease in ionic conductance, leading to a decrease in the cycle characteristic and output characteristic of the non-aqueous electrolyte battery. On the other hand, when the concentration exceeds 2.5 mol/L, the viscosity of the electrolyte solution for a non-aqueous electrolyte battery is increased, which may decrease the ionic conductance. Accordingly, there is a risk of lowering the cycle characteristic and the output characteristic of the non-aqueous electrolyte battery.

When a large amount of the solute (s) is dissolved at once in a non-aqueous solvent, the liquid temperature may increase because of the heat of the dissolution of the solute(s). If the liquid temperature increases significantly, the decomposition of the fluorine-containing electrolyte salt is accelerated and thus hydrogen fluoride may be generated. Hydrogen fluoride causes deterioration in battery performance and thus is not preferred. Although the liquid temperature at which the solute(s) is dissolved in a non-aqueous solvent is not particularly limited, the temperature ranges preferably −20° C. to 80° C., and more preferably 0° C. to 60° C.

As stated above, the constitutional components to be contained in the electrolyte solution for a non-aqueous electrolyte battery of the present invention have been explained. However, as long as the gist of the present invention is not impaired, any kinds of additives which have been generally used in an electrolyte solution for a non-aqueous electrolyte battery may be added at any ratio to the electrolyte solution for a non-aqueous electrolyte battery of the present invention. Specific examples thereof include compounds having an effect of preventing overcharge, an effect of forming a negative electrode film and an effect of protecting a positive electrode, such as cyclohexylbenzene, biphenyl, t-butylbenzene, vinylene carbonate, vinyl ethylene carbonate, difluoroanisole, fluoroethylene carbonate, propane sultone, succinonitrile and dimethyl vinylene carbonate. Moreover, as used in a non-aqueous electrolyte battery referred to as a lithium polymer battery, an electrolyte solution for a non-aqueous electrolyte battery can be pseudo-solidified with a gelling agent or a cross-linked polymer and then used.

Next, the structure or composition of the non-aqueous electrolyte battery of the present invention will be explained. The non-aqueous electrolyte battery of the present invention is characterized by the use of the above electrolyte solution for a non-aqueous electrolyte battery of the present invention. Any kinds of components which constitute non-aqueous electrolyte batteries other than the present non-aqueous electrolyte and which have been generally used in non-aqueous electrolyte batteries may be also used for the present non-aqueous electrolyte battery. Specifically, such components include a positive electrode and a negative electrode capable of occluding and releasing cations, a collector, a separator, and a container.

Materials for negative electrodes may not be particularly limited. They include, in the case of a lithium battery and a lithium ion battery, a lithium metal, an alloy of a lithium metal and another metal, or intermetallic compounds, various kinds of carbon materials (e.g., artificial graphite and natural graphite), a metal oxide, a metal nitride, tin (elemental substance), a tin compound, silicon (elemental substance), a silicon compound, an activated carbon, and a conductive polymer.

Examples of carbon materials include easily graphitizable carbon, hardly graphitizable carbon (hard carbon) having the interplanar spacing of plane (002) of 0.37 nm or more, and graphite having the interplanar spacing of plane (002) of 0.34 nm or less. More specific examples thereof include pyrolytic carbon, cokes, glassy carbon fibers, organic polymer compound fired bodies, activated carbon or carbon black. Of these, cokes include a pitch coke, a needle coke ora petroleum coke. An organic polymer compound fired body is referred to as a product produced by burning a phenol resin, a furan resin or the like at an appropriate temperature, followed by carbonization. Carbon materials are preferred since the crystal structure remains almost unchanged after the occlusion and release of lithium, so that higher energy density and excellent cycle characteristic can be obtained. In addition, the shape of a carbon material may be fibrous, spherical, granular or squamous. Furthermore, amorphous carbon or a graphite material whose surface is coated with amorphous carbon, is more preferred since the reactivity between the material surface and the electrolyte solution decreases.

Materials for positive electrodes to be used herein are not particularly limited. In the case of a lithium battery and a lithium ion battery, there can be used lithium-containing transition metal composite oxides such as $LiCoO_2$, $LiNiO_2$, $LiMnO_2$, and $LiMn_2O_4$, those lithium-containing transition metal composite oxides wherein a plurality of transition metals such as Co, Mn and Ni are mixed, those lithium-containing transition metal composite oxides wherein a part of the transition metals is replaced with a metal other than the transition metals, phosphate compounds of transition metals referred to as olivine such as $LiFePO_4$, $LiCoPO_4$, and $LiMnPO_4$, oxides such as $TiO_2$, $V_2O_5$ and $MoO_3$, sulfides such as $TiS_2$ and FeS, or conducting polymers such as polyacetylene, polyparaphenylene, polyaniline and polypyrrole, activated carbon, polymers that generate radicals, and carbon materials.

To a positive electrode or negative electrode material, acetylene black, Ketjen black, carbon fibers, or graphite as a conductive additive and polytetrafluoroethylene, polyvinylidene fluoride, SBR resin, or the like are added as a binder material, and then the resultant mixture is formed into a sheet, so that an electrode sheet can be produced.

As a separator for preventing the contact between a positive electrode and a negative electrode, a nonwoven fabric or porous sheet made of polypropylene, polyethylene, paper, and glass fibers is used.

A non-aqueous electrolyte battery formed to have a coin shape, cylindrical shape, square shape, laminated aluminum sheet form, or the like is assembled with each of the above components.

EXAMPLES

The present invention will be more specifically explained with reference to Examples, but the scope of the present invention is not limited to these Examples.

Preparation of Non-aqueous Electrolyte Solution $LiPF_6$ as a solute was dissolved in a mixed solvent containing ethylene carbonate, propylene carbonate, dimethyl carbonate and ethyl methyl carbonate at a volume ratio of 2:1:4:3 as a non-aqueous solvent, so that the concentration of the salute was set at 1.0 mol/L. Then, the compound No.2 as the first compound was added to the mixed solvent so as to achieve a concentration of 0.5% by mass and a lithium salt of the compound No.15 as the second compound was added to the mixed solvent so as to achieve a concentration of 1.0% by mass, followed by stirring, to prepare an electrolyte solution No.1. In this case, the above preparation was performed while maintaining the liquid temperature at 25° C. Table 1 shows the conditions for preparation of the electrolyte solution No.1.

Electrolyte solutions No.2 to 129 were also prepared in the same manner as above, except that the type and the concentration of the first compound, the type and the concentration of the second compound, and the type of the counter cation were changed as shown in Table 1 and Table 2. In this case, compounds No.51 to 53 used as the first compound in preparation of the electrolyte solutions No.117 to 119 and anions of the compounds No.54 to 63 used as the second compound in preparation of the electrolyte solutions No.120 to 129 are shown.

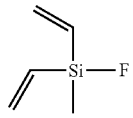

Compound No. 51

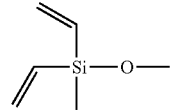

Compound No. 52

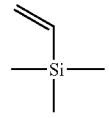

Compound No. 53

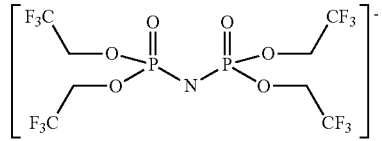

Compound No. 54

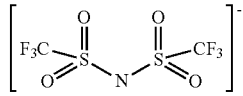

Compound No. 55

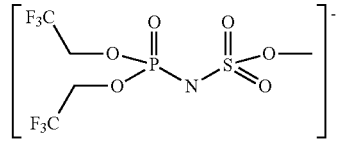

Compound No. 56

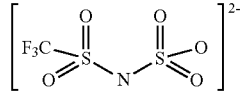

Compound No. 57

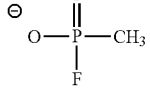

Compound No. 58

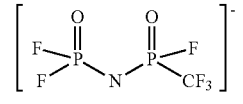

Compound No. 59

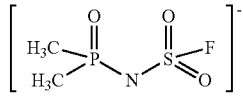

Compound No. 60

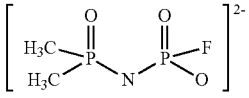

Compound No. 61

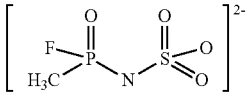

Compound No. 62

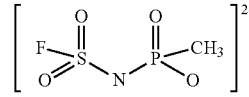

Compound No. 63

Example 1-1

A cell was prepared using the electrolyte solution No.1 as a non-aqueous electrolyte solution, $LiNi_{1/3}Mn_{1/3}CO_{1/3}O_2$ as a positive electrode material, and graphite as a negative electrode material. The cell was actually evaluated for a high-temperature cycle characteristic, a high-temperature storage characteristic, and a low-temperature output characteristic of the battery. A test cell was prepared as follows.

$LiNi_{1/3}Mn_{1/3}Co_{1/3}O_2$ powder (90% by mass) was mixed with 5% by mass of polyvinylidene fluoride (PVDF) as a binder and 5% by mass of acetylene black as a conductive additive. N-methylpyrrolidone was further added to the mixture and then the resultant mixture was formed into a paste. The paste was applied onto an aluminum foil, and then the foil was dried, thereby preparing a positive electrode body for a test. Graphite powder (90% by mass) was mixed with 10% by mass of PVDF as a binder and then N-methylpyrrolidone was further added the resultant mixture to form a slurry. The slurry was applied onto a copper foil, and then the foil was dried at 150° C. for 12 hours, thereby obtaining a negative electrode body for the test. A polyethylene separator was soaked with the electrolyte solution, so as to assemble a 100 mAh cell armored with an aluminum laminate.

A charge and discharge test was conducted using the cells prepared by the above methods, and evaluation of high-temperature cycle characteristics, high-temperature storage characteristics, and low-temperature output characteristics was performed by a method described below. Evaluation results are shown in Table 3.

High-temperature Cycle Characteristic Test

A charge and discharge test was conducted at an ambient temperature of 50° C. to evaluate a cycle characteristic. Charging was performed up to 4.3 V, and discharging was performed to 3.0 V, and then a charge and discharge cycle was repeated at a current density of 1.9 mA/cm$^2$. The cells were evaluated for a degree of deterioration based on a discharge capacity maintenance % after 200 cycles (evaluation of a cycle characteristic). The discharge capacity maintenance % was determined by the following formula.

<Discharge Capacity Maintenance % After 200 cycles>

Discharge capacity maintenance (%)=(discharge capacity after 200 cycles/initial discharge capacity)×100

The values of the discharge capacity maintenance % after 200 cycles shown in Table 3 are values relative to the value of the discharge capacity maintenance % after 200 cycles determined for Comparative example 1-1 designated as 100.

High-temperature Storage Characteristic Test

After the cycle test, charging was performed by a constant voltage and constant current method at an ambient temperature of 25° C. and a current density of 0.38 mA/cm$^2$ to an upper limit charging voltage of 4.3 V, followed by storage at an ambient temperature of 50° C. for 10 days. Subsequently, discharging was performed with a constant current density of 0.38 mA/cm$^2$ to a discharge end voltage of 3.0 V. The proportion of a discharge capacity to an initial discharge capacity (a value of a discharge capacity measured after the cycle test and before storage at 50° C.) was defined as the remaining capacity proportion and was used to evaluate a storage characteristic of the cells. The values of a remaining capacity proportion shown in Table 3 are values relative to the remaining capacity proportion determined for Comparative example 1-1 designated as 100.

Low-temperature Output Characteristic Test

After the storage test, charging was performed by a constant voltage and constant current method at an ambient temperature of 25° C. and a current density of 0.38 mA/cm$^2$ to an upper limit charging voltage of 4.3 V. Then, discharging was performed at an ambient temperature of −30° C. with a current density of 9.5 mA/cm$^2$ to a lower limit discharging voltage of 3.0 V. The average discharge voltage at this time was measured. The values of the average discharge voltage shown in Table 2 are values relative to the average discharge voltage determined for Comparative example 1-1 designated as 100.

Examples 1-2 to 1-65, Comparative Examples 1-1 to 1-64

In the same manner as in Example 1-1, cells were prepared respectively using the electrolyte solutions Nos.2 to 129 instead of the electrolyte solution No.1 and evaluated for a high-temperature cycle characteristic, high-temperature storage characteristic, and low-temperature output characteristic. Evaluation results are shown in Table 3 and Table 4.

TABLE 1

|  | First compound | | Second compound | | |
|---|---|---|---|---|---|
|  | Compound No. | Concentration [% by mass] | Compound No. | Counter cation | Concentration [% by mass] |
| Electrolyte solution No. 1 | No. 2 | 0.5 | No. 15 | Li$^+$ | 1.0 |
| Electrolyte solution No. 2 |  | 0.5 |  |  | 0.005 |
| Electrolyte solution No. 3 |  | 0.5 |  |  | 0.05 |
| Electrolyte solution No. 4 |  | 0.5 |  |  | 0.1 |
| Electrolyte solution No. 5 |  | 0.5 |  |  | 0.5 |
| Electrolyte solution No. 6 |  | 0.5 |  |  | 2.0 |
| Electrolyte solution No. 7 |  | 0.5 |  |  | 10.0 |
| Electrolyte solution No. 8 |  | 1.0 |  |  | 1.0 |
| Electrolyte solution No. 9 |  | 0.005 |  |  | 1.0 |
| Electrolyte solution No. 10 |  | 0.05 |  |  | 1.0 |
| Electrolyte solution No. 11 |  | 0.1 |  |  | 1.0 |
| Electrolyte solution No. 12 |  | 2.0 |  |  | 1.0 |
| Electrolyte solution No. 13 |  | 10.0 |  |  | 1.0 |
| Electrolyte solution No. 14 | No. 1 | 0.5 |  |  | 1.0 |

TABLE 1-continued

|  | First compound | | Second compound | | |
|---|---|---|---|---|---|
|  | Compound No. | Concentration [% by mass] | Compound No. | Counter cation | Concentration [% by mass] |
| Electrolyte solution No. 15 | No. 3 | 0.5 | | | 1.0 |
| Electrolyte solution No. 16 | No. 4 | 0.5 | | | 1.0 |
| Electrolyte solution No. 17 | No. 5 | 0.5 | | | 1.0 |
| Electrolyte solution No. 18 | No. 6 | 0.5 | | | 1.0 |
| Electrolyte solution No. 19 | No. 7 | 0.5 | | | 1.0 |
| Electrolyte solution No. 20 | No. 8 | 0.5 | | | 1.0 |
| Electrolyte solution No. 21 | No. 9 | 0.5 | | | 1.0 |
| Electrolyte solution No. 22 | No. 10 | 0.5 | | | 1.0 |
| Electrolyte solution No. 23 | No. 11 | 0.5 | | | 1.0 |
| Electrolyte solution No. 24 | No. 12 | 0.5 | | | 1.0 |
| Electrolyte solution No. 25 | No. 13 | 0.5 | | | 1.0 |
| Electrolyte solution No. 26 | No. 2 | 0.5 | No. 14 | | 1.0 |
| Electrolyte solution No. 27 | | 0.5 | No. 16 | | 1.0 |
| Electrolyte solution No. 28 | | 0.5 | No. 17 | | 1.0 |
| Electrolyte solution No. 29 | | 0.5 | No. 18 | | 1.0 |
| Electrolyte solution No. 30 | | 0.5 | No. 19 | | 1.0 |
| Electrolyte solution No. 31 | | 0.5 | No. 20 | | 1.0 |
| Electrolyte solution No. 32 | | 0.5 | No. 21 | | 1.0 |
| Electrolyte solution No. 33 | | 0.5 | No. 22 | | 1.0 |
| Electrolyte solution No. 34 | | 0.5 | No. 23 | | 1.0 |
| Electrolyte solution No. 35 | | 0.5 | No. 24 | | 1.0 |
| Electrolyte solution No. 36 | | 0.5 | No. 25 | | 1.0 |
| Electrolyte solution No. 37 | | 0.5 | No. 26 | | 1.0 |
| Electrolyte solution No. 38 | | 0.5 | No. 27 | | 1.0 |
| Electrolyte solution No. 39 | | 0.5 | No. 28 | | 1.0 |
| Electrolyte solution No. 40 | | 0.5 | No. 29 | | 1.0 |
| Electrolyte solution No. 41 | | 0.5 | No. 30 | | 1.0 |
| Electrolyte solution No. 42 | | 0.5 | No. 31 | | 1.0 |
| Electrolyte solution No. 43 | | 0.5 | No. 32 | | 1.0 |
| Electrolyte solution No. 44 | | 0.5 | No. 33 | | 1.0 |
| Electrolyte solution No. 45 | | 0.5 | No. 34 | | 1.0 |
| Electrolyte solution No. 46 | | 0.5 | No. 35 | | 1.0 |
| Electrolyte solution No. 47 | | 0.5 | No. 36 | | 1.0 |
| Electrolyte solution No. 48 | | 0.5 | No. 37 | $2Li^+$ | 1.0 |
| Electrolyte solution No. 49 | | 0.5 | No. 38 | | 1.0 |
| Electrolyte solution No. 50 | | 0.5 | No. 39 | | 1.0 |
| Electrolyte solution No. 51 | | 0.5 | No. 40 | | 1.0 |
| Electrolyte solution No. 52 | | 0.5 | No. 41 | | 1.0 |
| Electrolyte solution No. 53 | | 0.5 | No. 42 | | 1.0 |
| Electrolyte solution No. 54 | | 0.5 | No. 43 | | 1.0 |
| Electrolyte solution No. 55 | | 0.5 | No. 44 | | 1.0 |
| Electrolyte solution No. 56 | | 0.5 | No. 45 | | 1.0 |
| Electrolyte solution No. 57 | | 0.5 | No. 46 | | 1.0 |
| Electrolyte solution No. 58 | | 0.5 | No. 47 | | 1.0 |
| Electrolyte solution No. 59 | | 0.5 | No. 48 | | 1.0 |
| Electrolyte solution No. 60 | | 0.5 | No. 49 | | 1.0 |
| Electrolyte solution No. 61 | | 0.5 | No. 50 | | 1.0 |
| Electrolyte solution No. 62 | | 0.5 | No. 15 | $Na^+$ | 1.0 |

TABLE 1-continued

| | First compound | | Second compound | | |
|---|---|---|---|---|---|
| | Compound No. | Concentration [% by mass] | Compound No. | Counter cation | Concentration [% by mass] |
| Electrolyte solution No. 63 | | 0.5 | | K⁺ | 1.0 |
| Electrolyte solution No. 64 | | 0.5 | | $(C_2H_5)_4N^+$ | 1.0 |
| Electrolyte solution No. 65 | | 0.5 | | $(C_2H_5)_4P^+$ | 1.0 |

TABLE 2

| | First compound | | Second compound | | |
|---|---|---|---|---|---|
| | Compound No. | Concentration [% by mass] | Compound No. | Counter cation | Concentration [% by mass] |
| Electrolyte solution No. 66 | None | — | None | — | — |
| Electrolyte solution No. 67 | No. 1 | 0.5 | | | — |
| Electrolyte solution No. 68 | No. 2 | 0.5 | | | — |
| Electrolyte solution No. 69 | No. 3 | 0.5 | | | — |
| Electrolyte solution No. 70 | No. 4 | 0.5 | | | — |
| Electrolyte solution No. 71 | No. 5 | 0.5 | | | — |
| Electrolyte solution No. 72 | No. 6 | 0.5 | | | — |
| Electrolyte solution No. 73 | No. 7 | 0.5 | | | — |
| Electrolyte solution No. 74 | No. 8 | 0.5 | | | — |
| Electrolyte solution No. 75 | No. 9 | 0.5 | | | — |
| Electrolyte solution No. 76 | No. 10 | 0.5 | | | — |
| Electrolyte solution No. 77 | No. 11 | 0.5 | | | — |
| Electrolyte solution No. 78 | No. 12 | 0.5 | | | — |
| Electrolyte solution No. 79 | No. 13 | 0.5 | | | — |
| Electrolyte solution No. 80 | None | — | No. 14 | Li⁺ | 1.0 |
| Electrolyte solution No. 81 | | — | No. 15 | | 1.0 |
| Electrolyte solution No. 82 | | — | No. 16 | | 1.0 |
| Electrolyte solution No. 83 | | — | No. 17 | | 1.0 |
| Electrolyte solution No. 84 | | — | No. 18 | | 1.0 |
| Electrolyte solution No. 85 | | — | No. 19 | | 1.0 |
| Electrolyte solution No. 86 | | — | No. 20 | | 1.0 |
| Electrolyte solution No. 87 | | — | No. 21 | | 1.0 |
| Electrolyte solution No. 88 | | — | No. 22 | | 1.0 |
| Electrolyte solution No. 89 | | — | No. 23 | | 1.0 |
| Electrolyte solution No. 90 | | — | No. 24 | | 1.0 |
| Electrolyte solution No. 91 | | — | No. 25 | | 1.0 |
| Electrolyte solution No. 91 | | — | No. 26 | | 1.0 |
| Electrolyte solution No. 93 | | — | No. 27 | | 1.0 |
| Electrolyte solution No. 94 | | — | No. 28 | | 1.0 |
| Electrolyte solution No. 95 | | — | No. 29 | | 1.0 |
| Electrolyte solution No. 96 | | — | No. 30 | | 1.0 |
| Electrolyte solution No. 97 | | — | No. 31 | | 1.0 |
| Electrolyte solution No. 98 | | — | No. 32 | | 1.0 |
| Electrolyte solution No. 99 | | — | No. 33 | | 1.0 |
| Electrolyte solution No. 100 | | — | No. 34 | | 1.0 |
| Electrolyte solution No. 101 | | — | No. 35 | | 1.0 |
| Electrolyte solution No. 102 | | — | No. 36 | | 1.0 |
| Electrolyte solution No. 103 | | — | No. 37 | 2Li⁺ | 1.0 |
| Electrolyte solution No. 104 | | — | No. 38 | | 1.0 |
| Electrolyte solution No. 105 | | — | No. 39 | | 1.0 |
| Electrolyte solution No. 106 | | — | No. 40 | | 1.0 |

TABLE 2-continued

| | First compound | | Second compound | | |
|---|---|---|---|---|---|
| | Compound No. | Concentration [% by mass] | Compound No. | Counter cation | Concentration [% by mass] |
| Electrolyte solution No. 107 | — | | No. 41 | | 1.0 |
| Electrolyte solution No. 108 | — | | No. 42 | | 1.0 |
| Electrolyte solution No. 109 | — | | No. 43 | | 1.0 |
| Electrolyte solution No. 110 | — | | No. 44 | | 1.0 |
| Electrolyte solution No. 111 | — | | No. 45 | | 1.0 |
| Electrolyte solution No. 112 | — | | No. 46 | | 1.0 |
| Electrolyte solution No. 113 | — | | No. 47 | | 1.0 |
| Electrolyte solution No. 114 | — | | No. 48 | | 1.0 |
| Electrolyte solution No. 115 | — | | No. 49 | | 1.0 |
| Electrolyte solution No. 116 | — | | No. 50 | | 1.0 |
| Electrolyte solution No. 117 | No. 51 | 0.5 | No. 15 | Li$^+$ | 1.0 |
| Electrolyte solution No. 118 | No. 52 | 0.5 | | | 1.0 |
| Electrolyte solution No. 119 | No. 53 | 0.5 | | | 1.0 |
| Electrolyte solution No. 120 | No. 2 | 0.5 | No. 54 | | 1.0 |
| Electrolyte solution No. 121 | | 0.5 | No. 55 | | 1.0 |
| Electrolyte solution No. 122 | | 0.5 | No. 56 | | 1.0 |
| Electrolyte solution No. 123 | | 0.5 | No. 57 | 2Li$^+$ | 1.0 |
| Electrolyte solution No. 124 | | 0.5 | No. 58 | Li$^+$ | 1.0 |
| Electrolyte solution No. 125 | | 0.5 | No. 59 | | 1.0 |
| Electrolyte solution No. 126 | | 0.5 | No. 60 | | 1.0 |
| Electrolyte solution No. 127 | | 0.5 | No. 61 | 2Li$^+$ | 1.0 |
| Electrolyte solution No. 128 | | 0.5 | No. 62 | | 1.0 |
| Electrolyte solution No. 129 | | 0.5 | No. 63 | | 1.0 |

TABLE 3

| | Electrolyte solution No. | Positive electrode Active material | Negative electrode Active material | Discharge capacity maintenance* [%] After 200 cycles | Remaining capacity proportion* [%] | Average discharge voltage* [%] |
|---|---|---|---|---|---|---|
| Example 1-1 | No. 1 | LiNi$_{1/3}$Mn$_{1/3}$Co$_{1/3}$O$_2$ | Graphite | 138 | 151 | 106 |
| Example 1-2 | No. 2 | | | 122 | 143 | 103 |
| Example 1-3 | No. 3 | | | 124 | 144 | 104 |
| Example 1-4 | No. 4 | | | 130 | 146 | 105 |
| Example 1-5 | No. 5 | | | 135 | 149 | 105 |
| Example 1-6 | No. 6 | | | 132 | 139 | 106 |
| Example 1-7 | No. 7 | | | 123 | 137 | 105 |
| Example 1-8 | No. 8 | | | 137 | 151 | 105 |
| Example 1-9 | No. 9 | | | 105 | 107 | 103 |
| Example 1-10 | No. 10 | | | 110 | 111 | 104 |
| Example 1-11 | No. 11 | | | 113 | 115 | 104 |
| Example 1-12 | No. 12 | | | 137 | 149 | 104 |
| Example 1-13 | No. 13 | | | 133 | 140 | 103 |
| Example 1-14 | No. 14 | | | 130 | 137 | 105 |
| Example 1-15 | No. 15 | | | 132 | 136 | 106 |
| Example 1-16 | No. 16 | | | 127 | 133 | 105 |
| Example 1-17 | No. 17 | | | 125 | 130 | 105 |
| Example 1-18 | No. 18 | | | 129 | 133 | 104 |
| Example 1-19 | No. 19 | | | 137 | 150 | 105 |
| Example 1-20 | No. 20 | | | 131 | 134 | 104 |
| Example 1-21 | No. 21 | | | 130 | 134 | 104 |
| Example 1-22 | No. 22 | | | 130 | 133 | 104 |
| Example 1-23 | No. 23 | | | 129 | 133 | 104 |
| Example 1-24 | No. 24 | | | 129 | 132 | 104 |
| Example 1-25 | No. 25 | | | 129 | 130 | 103 |
| Example 1-26 | No. 26 | | | 126 | 129 | 104 |
| Example 1-27 | No. 27 | | | 136 | 147 | 104 |
| Example 1-28 | No. 28 | | | 135 | 147 | 104 |
| Example 1-29 | No. 29 | | | 133 | 145 | 104 |

TABLE 3-continued

|  | Electrolyte solution No. | Positive electrode Active material | Negative electrode Active material | Discharge capacity maintenance* [%] After 200 cycles | Remaining capacity proportion* [%] | Average discharge voltage* [%] |
|---|---|---|---|---|---|---|
| Example 1-30 | No. 30 |  |  | 133 | 144 | 103 |
| Example 1-31 | No. 31 |  |  | 135 | 146 | 104 |
| Example 1-32 | No. 32 |  |  | 136 | 145 | 105 |
| Example 1-33 | No. 33 |  |  | 130 | 131 | 103 |
| Example 1-34 | No. 34 |  |  | 131 | 131 | 103 |
| Example 1-35 | No. 35 |  |  | 127 | 129 | 104 |
| Example 1-36 | No. 36 |  |  | 135 | 146 | 103 |
| Example 1-37 | No. 37 |  |  | 128 | 127 | 104 |
| Example 1-38 | No. 38 |  |  | 127 | 128 | 103 |
| Example 1-39 | No. 39 |  |  | 127 | 130 | 103 |
| Example 1-40 | No. 40 |  |  | 126 | 130 | 103 |
| Example 1-41 | No. 41 |  |  | 127 | 131 | 103 |
| Example 1-42 | No. 42 |  |  | 121 | 114 | 102 |
| Example 1-43 | No. 43 |  |  | 126 | 128 | 103 |
| Example 1-44 | No. 44 |  |  | 112 | 110 | 102 |
| Example 1-45 | No. 45 |  |  | 113 | 112 | 103 |
| Example 1-46 | No. 46 |  |  | 113 | 111 | 102 |
| Example 1-47 | No. 47 |  |  | 108 | 105 | 102 |
| Example 1-48 | No. 48 |  |  | 137 | 149 | 104 |
| Example 1-49 | No. 49 |  |  | 128 | 130 | 103 |
| Example 1-50 | No. 50 |  |  | 127 | 130 | 102 |
| Example 1-51 | No. 51 |  |  | 122 | 115 | 102 |
| Example 1-52 | No. 52 |  |  | 125 | 127 | 103 |
| Example 1-53 | No. 53 |  |  | 120 | 113 | 102 |
| Example 1-54 | No. 54 |  |  | 105 | 105 | 102 |
| Example 1-55 | No. 55 |  |  | 107 | 106 | 102 |
| Example 1-56 | No. 56 |  |  | 107 | 107 | 102 |
| Example 1-57 | No. 57 |  |  | 123 | 127 | 104 |
| Example 1-58 | No. 58 |  |  | 108 | 109 | 102 |
| Example 1-59 | No. 59 |  |  | 107 | 108 | 104 |
| Example 1-60 | No. 60 |  |  | 110 | 109 | 103 |
| Example 1-61 | No. 61 |  |  | 103 | 103 | 102 |
| Example 1-62 | No. 62 |  |  | 130 | 149 | 106 |
| Example 1-63 | No. 63 |  |  | 130 | 150 | 106 |
| Example 1-64 | No. 64 |  |  | 129 | 151 | 105 |
| Example 1-65 | No. 65 |  |  | 128 | 150 | 105 |

*Relative value when the value of Comparative example 1-1 is designated as 100.

TABLE 4

|  | Electrolyte solution No. | Positive electrode Active material | Negative electrode Active material | Discharge capacity maintenance* [%] After 200 cycles | Remaining capacity proportion* [%] | Average discharge voltage* [%] |
|---|---|---|---|---|---|---|
| Comparative example 1-1 | No. 66 | $LiNi_{1/3}Mn_{1/3}Co_{1/3}O_2$ | Graphite | 100 | 100 | 100 |
| Comparative example 1-2 | No. 67 |  |  | 95 | 93 | 97 |
| Comparative example 1-3 | No. 68 |  |  | 100 | 99 | 96 |
| Comparative example 1-4 | No. 69 |  |  | 98 | 98 | 95 |
| Comparative example 1-5 | No. 70 |  |  | 95 | 94 | 95 |
| Comparative example 1-6 | No. 71 |  |  | 92 | 91 | 95 |
| Comparative example 1-7 | No. 72 |  |  | 94 | 92 | 94 |
| Comparative example 1-8 | No. 73 |  |  | 99 | 100 | 94 |
| Comparative example 1-9 | No. 74 |  |  | 98 | 97 | 97 |
| Comparative example 1-10 | No. 75 |  |  | 96 | 96 | 97 |
| Comparative example 1-11 | No. 76 |  |  | 97 | 96 | 97 |
| Comparative example 1-12 | No. 77 |  |  | 96 | 97 | 97 |
| Comparative example 1-13 | No. 78 |  |  | 94 | 95 | 96 |
| Comparative example 1-14 | No. 79 |  |  | 92 | 92 | 95 |

TABLE 4-continued

| | Electrolyte solution No. | Positive electrode Active material | Negative electrode Active material | Discharge capacity maintenance* [%] After 200 cycles | Remaining capacity proportion* [%] | Average discharge voltage* [%] |
|---|---|---|---|---|---|---|
| Comparative example 1-15 | No. 80 | | | 104 | 97 | 98 |
| Comparative example 1-16 | No. 81 | | | 102 | 91 | 100 |
| Comparative example 1-17 | No. 82 | | | 102 | 93 | 98 |
| Comparative example 1-18 | No. 83 | | | 103 | 94 | 97 |
| Comparative example 1-19 | No. 84 | | | 102 | 90 | 97 |
| Comparative example 1-20 | No. 85 | | | 101 | 88 | 97 |
| Comparative example 1-21 | No. 86 | | | 101 | 90 | 99 |
| Comparative example 1-22 | No. 87 | | | 102 | 96 | 96 |
| Comparative example 1-23 | No. 88 | | | 103 | 97 | 96 |
| Comparative example 1-24 | No. 89 | | | 102 | 92 | 96 |
| Comparative example 1-25 | No. 90 | | | 101 | 89 | 96 |
| Comparative example 1-26 | No. 91 | | | 101 | 90 | 99 |
| Comparative example 1-27 | No. 92 | | | 102 | 92 | 97 |
| Comparative example 1-28 | No. 93 | | | 102 | 93 | 96 |
| Comparative example 1-29 | No. 94 | | | 103 | 94 | 97 |
| Comparative example 1-30 | No. 95 | | | 104 | 93 | 97 |
| Comparative example 1-31 | No. 96 | | | 104 | 92 | 96 |
| Comparative example 1-32 | No. 97 | | | 103 | 87 | 96 |
| Comparative example 1-33 | No. 98 | | | 102 | 93 | 97 |
| Comparative example 1-34 | No. 99 | | | 103 | 94 | 96 |
| Comparative example 1-35 | No. 100 | | | 102 | 95 | 96 |
| Comparative example 1-36 | No. 101 | | | 102 | 93 | 96 |
| Comparative example 1-37 | No. 102 | | | 103 | 92 | 96 |
| Comparative example 1-38 | No. 103 | | | 104 | 97 | 99 |
| Comparative example 1-39 | No. 104 | | | 103 | 95 | 97 |
| Comparative example 1-40 | No. 105 | | | 102 | 96 | 97 |
| Comparative example 1-41 | No. 106 | | | 101 | 93 | 97 |
| Comparative example 1-42 | No. 107 | | | 101 | 92 | 97 |
| Comparative example 1-43 | No. 108 | | | 101 | 89 | 96 |
| Comparative example 1-44 | No. 109 | | | 102 | 90 | 96 |
| Comparative example 1-45 | No. 110 | | | 102 | 93 | 96 |
| Comparative example 1-46 | No. 111 | | | 101 | 92 | 96 |
| Comparative example 1-47 | No. 112 | | | 102 | 94 | 97 |
| Comparative example 1-48 | No. 113 | | | 102 | 94 | 96 |
| Comparative example 1-49 | No. 114 | | | 101 | 90 | 96 |
| Comparative example 1-50 | No. 115 | | | 101 | 88 | 96 |
| Comparative example 1-51 | No. 116 | | | 101 | 90 | 96 |
| Comparative example 1-52 | No. 117 | | | 99 | 100 | 94 |

TABLE 4-continued

| | Electrolyte solution No. | Positive electrode Active material | Negative electrode Active material | Discharge capacity maintenance* [%] After 200 cycles | Remaining capacity proportion* [%] | Average discharge voltage* [%] |
|---|---|---|---|---|---|---|
| Comparative example 1-53 | No. 118 | | | 71 | 82 | 96 |
| Comparative example 1-54 | No. 119 | | | 93 | 89 | 97 |
| Comparative example 1-55 | No. 120 | | | 100 | 95 | 98 |
| Comparative example 1-56 | No. 121 | | | 101 | 88 | 99 |
| Comparative example 1-57 | No. 122 | | | 100 | 94 | 97 |
| Comparative example 1-58 | No. 123 | | | 102 | 91 | 97 |
| Comparative example 1-59 | No. 124 | | | 100 | 85 | 95 |
| Comparative example 1-60 | No. 125 | | | 101 | 91 | 95 |
| Comparative example 1-61 | No. 126 | | | 102 | 87 | 94 |
| Comparative example 1-62 | No. 127 | | | 101 | 89 | 95 |
| Comparative example 1-63 | No. 128 | | | 102 | 93 | 96 |
| Comparative example 1-64 | No. 129 | | | 102 | 93 | 96 |

*Relative value when the value of Comparative example 1-1 is designated as 100.

The above results confirm that a high-temperature cycle characteristic, high-temperature storage characteristic, and low-temperature output characteristic are improved by combining the first compound with the second compound, as compared with Comparative examples 1-2 to 1-14 wherein the first compound was used alone. Similarly, the above results confirm that a high-temperature cycle characteristic, high-temperature storage characteristic, and low-temperature output characteristic were improved by combining the first compound with the second compound, as compared with Comparative examples 1-15 to 1-51 wherein the second compound was used alone.

In the case of Comparative examples 1-52 and 1-53 wherein $R^2$ of the first compound represented by general formula (1) is not a linear or branched $C_{1-10}$ alkyl group ($R^2$ in Comparative example 1-52 contained a fluorine group, and $R^2$ in Comparative example 1-53 contained a methoxy group), a low-temperature output characteristic was decreased and no improvement was confirmed in a high-temperature cycle characteristic or high-temperature storage characteristic. In the case of Comparative example 1-54 wherein the number of groups having a carbon-carbon unsaturated bond is 1 or less, no improvement was confirmed in a high-temperature cycle characteristic, high-temperature storage characteristic, or low-temperature output characteristic.

In the case of Comparative examples 1-55 to 1-58 wherein the second compound contains neither a P—F bond nor an S—F bond, no improvement was confirmed in a high-temperature cycle characteristic, high-temperature storage characteristic, or low-temperature output characteristic. In the case of Comparative examples 1-59 to 1-64 wherein the second compound contains a P—F bond or an S—F bond but does not have a structure whose substituent bonded to a P atom is a hydrocarbon group containing an intervening oxygen atom (such as an alkoxy group) and has a structure having a hydrocarbon group containing no intervening oxygen atom (such as an alkyl group), a low-temperature output characteristic was decreased and no improvement was confirmed in a high-temperature cycle characteristic or high-temperature storage characteristic.

The evaluation results will be explained below for the electrolyte solutions containing a typical first compound and a typical second compound in combination at a typical concentration also changing the types of positive electrodes, the types of negative electrodes, and the types of counter cations of the second compound. The tendencies similar to those as explained above were confirmed for the electrolyte solutions wherein the combinations of the first compound and the second compound and the concentrations thereof are different from those which will be described below.

Examples 2-1 to 2-43 and Comparative Examples 2-1 to 2-20

In Examples 2-1 to 2-43 and Comparative examples 2-1 to 2-20, as shown in Table 6, electrolyte solutions for non-aqueous electrolyte batteries were prepared, cells were prepared, and then the batteries were evaluated in the same manner as Example 1-1 except that the kinds of the negative electrode bodies and the kinds of the electrolyte solutions were changed. In this case, in Examples 2-1 to 2-13 and Comparative examples 2-1 to 2-5 wherein the negative electrode active material is $Li_4Ti_5O_{12}$, the negative electrode bodies were prepared by mixing 90% by mass of $Li_4Ti_5O_{12}$ powder with 5% by mass of PVDF as a binder and 5% by mass of acetylene black as a conductive additive, to which N-methylpyrrolidone was added, applying the thus obtained paste onto a copper foil, and then drying it. The charge end voltage was 2.8 V and the discharge end voltage was 1.5 V, when the batteries were evaluated. Furthermore, in Examples 2-14 to 2-30 and Comparative examples 2-6 to 2-15 wherein the negative electrode active material was graphite (containing silicon), the negative electrode body was prepared by mixing 81% by mass of graphite powder and 9% by mass of silicon powder with 5% by mass of PVDF as a binder and 5% by mass of acetylene black as a conductive additive, to which N-methylpyrrolidone was added, applying the thus obtained paste onto a copper foil, and then drying it. The charge end voltage and the discharge end voltage when the batteries were evaluated were the same as those in Example 1-1. Moreover, in Examples 2-31 to 2-43 and Comparative examples 2-16 to 2-20 wherein the negative electrode active material was hard carbon, the negative electrode body was prepared by mixing 90% by mass of hard carbon powder with 5% by mass of PVDF as a binder and 5% by mass of acetylene black as a conductive additive, to which N-methylpyrrolidone was added, applying the thus obtained paste onto a copper foil, and then drying it. The charge end voltage and the discharge end voltage when the batteries were evaluated were 4.2 V and 2.2 V, respectively.

The electrolyte solution used in Example 2-27 was prepared as follows. A mixed solvent containing ethylene carbonate, fluoroethylene carbonate, dimethyl carbonate, and ethyl methyl carbonate at a volume ratio of 2.5:0.5:4:3 was used as a non-aqueous solvent. $LiPF_6$ as a solute was dissolved in the solvent to achieve a concentration of 1.0 mol/L. Then, the compound No.2 as the first compound was added to the resultant solution so as to achieve a concentration of 0.5% by mass and a lithium salt of the compound No.15 as the second compound was added to the resultant solution so as to achieve a concentration of 1.0% by mass, followed by stirring, to prepare an electrolyte solution No.130. The above preparation was performed while maintaining the liquid temperature at 25° C. Table 5 shows the conditions for preparation of the electrolyte solution No.130. The electrolyte solutions No.131 to 138 were also prepared in the same manner as the electrolyte solution No.130, except that the kinds and the like of the first compound and the second compound were changed as shown in Table 5.

The evaluation results for a high-temperature cycle characteristic, high-temperature storage characteristic and low-temperature output characteristic are shown in Table 6. The evaluation results (the values of discharge capacity maintenance % after 200 cycles, the values of remaining capacity proportion, the values of average discharge voltage) of Examples 2-1 to 2-26, Examples 2-31 to 2-43, Comparative examples 2-1 to 2-10, and Comparative examples 2-16 to 2-20 in Table 6 are values relative to the evaluation results in the Comparative examples using the electrolyte solution No.66 designated as 100 in respect of each electrode constitution. The evaluation results (the values of discharge capacity maintenance % after 200 cycles, the values of remaining capacity proportion, the values of average discharge voltage) of Examples 2-27 to 2-30 and Comparative examples 2-11 to 2-15 in Table 6 are values relative to the evaluation results in the Comparative examples using the electrolyte solution No.134 designated as 100.

TABLE 5

| | First compound | | Second compound | | |
| --- | --- | --- | --- | --- | --- |
| | Compound No. | Concentration [% by mass] | Compound No. | Counter cation | Concentration [% by mass] |
| Electrolyte solution No. 130 | No. 2 | 0.5 | No. 15 | $Li^+$ | 1.0 |
| Electrolyte solution No. 131 | No. 7 | 0.5 | | | 1.0 |
| Electrolyte solution No. 132 | No. 2 | 0.5 | No. 14 | | 1.0 |
| Electrolyte solution No. 133 | No. 7 | 0.5 | | | 1.0 |
| Electrolyte solution No. 134 | None | — | None | — | — |
| Electrolyte solution No. 135 | No. 2 | 0.5 | | | — |
| Electrolyte solution No. 136 | No. 7 | 0.5 | | | — |
| Electrolyte solution No. 137 | None | — | No. 15 | $Li^+$ | 1.0 |
| Electrolyte solution No. 138 | | — | No. 14 | | 1.0 |

TABLE 6

| | Electrolyte solution No. | Positive electrode Active material | Negative electrode Active material | Discharge capacity maintenance* [%] After 200 cycles | Remaining capacity proportion* [%] | Average discharge voltage* [%] |
| --- | --- | --- | --- | --- | --- | --- |
| Example 2-1 | No. 1 | $LiNi_{1/3}Mn_{1/3}Co_{1/3}O_2$ | $Li_4Ti_5O_{12}$ | 119 | 125 | 105 |
| Example 2-2 | No. 19 | | | 119 | 124 | 105 |
| Example 2-3 | No. 26 | | | 113 | 114 | 103 |
| Example 2-4 | No. 28 | | | 118 | 123 | 104 |
| Example 2-5 | No. 36 | | | 117 | 123 | 103 |
| Example 2-6 | No. 38 | | | 114 | 114 | 102 |
| Example 2-7 | No. 40 | | | 113 | 114 | 102 |
| Example 2-8 | No. 43 | | | 112 | 113 | 102 |
| Example 2-9 | No. 46 | | | 106 | 105 | 103 |
| Example 2-10 | No. 48 | | | 108 | 123 | 104 |
| Example 2-11 | No. 52 | | | 113 | 113 | 104 |
| Example 2-12 | No. 57 | | | 112 | 114 | 103 |
| Example 2-13 | No. 61 | | | 102 | 101 | 102 |
| Comparative example 2-1 | No. 66 | | | 100 | 100 | 100 |
| Comparative example 2-2 | No. 68 | | | 99 | 99 | 97 |
| Comparative example 2-3 | No. 81 | | | 102 | 95 | 99 |

TABLE 6-continued

| | Electrolyte solution No. | Positive electrode Active material | Negative electrode Active material | Discharge capacity maintenance* [%] After 200 cycles | Remaining capacity proportion* [%] | Average discharge voltage* [%] |
|---|---|---|---|---|---|---|
| Comparative example 2-4 | No. 117 | | | 100 | 99 | 96 |
| Comparative example 2-5 | No. 121 | | | 96 | 94 | 100 |
| Example 2-14 | No. 1 | | Graphite (containing silicon) | 133 | 145 | 105 |
| Example 2-15 | No. 19 | | | 132 | 145 | 104 |
| Example 2-16 | No. 26 | | | 122 | 124 | 103 |
| Example 2-17 | No. 28 | | | 130 | 141 | 103 |
| Example 2-18 | No. 36 | | | 131 | 141 | 103 |
| Example 2-19 | No. 38 | | | 122 | 123 | 102 |
| Example 2-20 | No. 40 | | | 122 | 124 | 103 |
| Example 2-21 | No. 43 | | | 121 | 124 | 102 |
| Example 2-22 | No. 46 | | | 106 | 106 | 103 |
| Example 2-23 | No. 48 | | | 132 | 144 | 105 |
| Example 2-24 | No. 52 | | | 121 | 122 | 104 |
| Example 2-25 | No. 57 | | | 119 | 121 | 103 |
| Example 2-26 | No. 61 | | | 101 | 102 | 102 |
| Example 2-27 | No. 130 | | | 132 | 146 | 105 |
| Example 2-28 | No. 131 | | | 130 | 145 | 104 |
| Example 2-29 | No. 132 | | | 121 | 124 | 102 |
| Example 2-30 | No. 133 | | | 120 | 122 | 101 |
| Comparative example 2-6 | No. 66 | | | 100 | 100 | 100 |
| Comparative example 2-7 | No. 68 | | | 98 | 97 | 97 |
| Comparative example 2-8 | No. 81 | | | 101 | 89 | 98 |
| Comparative example 2-9 | No. 117 | | | 97 | 100 | 96 |
| Comparative example 2-10 | No. 121 | | | 94 | 91 | 100 |
| Comparative example 2-11 | No. 134 | | | 100 | 100 | 100 |
| Comparative example 2-12 | No. 135 | | | 99 | 98 | 96 |
| Comparative example 2-13 | No. 136 | | | 98 | 99 | 93 |
| Comparative example 2-14 | No. 137 | | | 102 | 93 | 98 |
| Comparative example 2-15 | No. 138 | | | 103 | 97 | 96 |
| Example 2-31 | No. 1 | | Hard carbon | 129 | 141 | 105 |
| Example 2-32 | No. 19 | | | 127 | 140 | 105 |
| Example 2-33 | No. 26 | | | 117 | 120 | 104 |
| Example 2-34 | No. 28 | | | 126 | 137 | 103 |
| Example 2-35 | No. 36 | | | 125 | 136 | 103 |
| Example 2-36 | No. 38 | | | 118 | 118 | 103 |
| Example 2-37 | No. 40 | | | 116 | 120 | 102 |
| Example 2-38 | No. 43 | | | 116 | 119 | 102 |
| Example 2-39 | No. 46 | | | 105 | 104 | 104 |
| Example 2-40 | No. 48 | | | 126 | 139 | 104 |
| Example 2-41 | No. 52 | | | 114 | 118 | 103 |
| Example 2-42 | No. 57 | | | 114 | 117 | 103 |
| Example 2-43 | No. 61 | | | 102 | 102 | 103 |
| Comparative example 2-16 | No. 66 | | | 100 | 100 | 100 |
| Comparative example 2-17 | No. 68 | | | 99 | 100 | 98 |
| Comparative example 2-18 | No. 81 | | | 102 | 92 | 99 |
| Comparative example 2-19 | No. 117 | | | 99 | 99 | 97 |
| Comparative example 2-20 | No. 121 | | | 96 | 91 | 99 |

*Relative value in each corresponding battery configuration, when the value of Comparative example wherein Electrolyte solution No. 66 was used is designated as 100.

(In Examples 2-27 to 2-30 and Comparative examples 2-11 to 2-15, the relative value when the value of Comparative example 2-11 is designated as 100.)

Examples 3-1 to 3-52 and Comparative Examples 3-1 to 3-20

In Examples 3-1 to 3-52 and Comparative examples 3-1 to 3-20, as shown in Tables 7 and 8, the electrolyte solutions for non-aqueous electrolyte batteries were prepared, cells were prepared, and then the batteries were evaluated in the same manner as in Example 1-1, except that the kinds of the positive electrode bodies and the negative electrode bodies, as well as the kinds of the electrolyte solutions were changed. In this case, the positive electrode body wherein the positive electrode active material is $LiCoO_2$ was prepared by mixing 90% by mass of $LiCoO_2$ powder with 5% by mass of PVDF as a binder and 5% by mass of acetylene black as a conductive additive, to which N-methylpyrrolidone was added, applying the thus obtained paste onto an aluminum foil, and then drying it. In Examples 3-1 to 3-13 and Comparative examples 3-1 to 3-5 wherein the negative electrode active material is graphite as in Example 1-1, the charge end voltage was 4.2 V and the discharge end voltage was 3.0 V, when the resultant batteries were evaluated. In Examples 3-14 to 3-26 and Comparative examples 3-6 to 3-10 wherein the negative electrode active material is $Li_4Ti_5O_{12}$ as in Example 2-1, the charge end voltage was 2.7 V and the discharge end voltage was 1.5 V, when the resultant batteries were evaluated. In Examples 3-27 to 3-39 and Comparative examples 3-11 to 3-15 wherein the negative electrode active material is graphite (containing silicon at 9% by mass) as in Example 2-14, the charge end voltage was 4.2 V and the discharge end voltage was 3.0 V, when the resultant batteries were evaluated. In Examples 3-40 to 3-52 and Comparative examples 3-16 to 3-20 wherein the negative electrode active material is hard carbon as in Example 2-31, the charge end voltage was 4.1 V and the discharge end voltage was 2.2 V, the resultant batteries were evaluated. The evaluation results for a high-temperature cycle characteristic, high-temperature storage characteristic and low-temperature output characteristic are shown in Tables 7 and 8. The evaluation results (the values of discharge capacity maintenance % after 200 cycles, the values of remaining capacity proportion, the values of average discharge voltage) in Tables 7 and 8 are values relative to the evaluation results of the Comparative examples using the electrolyte solution No.66 designated as 100 in respect of each electrode constitution.

TABLE 7

|  | Electrolyte solution No. | Positive electrode Active material | Negative electrode Active material | Discharge capacity maintenance* [%] After 200 cycles | Remaining capacity proportion* [%] | Average discharge voltage* [%] |
|---|---|---|---|---|---|---|
| Example 3-1 | No. 1 | $LiCoO_2$ | Graphite | 137 | 149 | 105 |
| Example 3-2 | No. 19 | | | 136 | 149 | 104 |
| Example 3-3 | No. 26 | | | 124 | 128 | 104 |
| Example 3-4 | No. 28 | | | 133 | 147 | 103 |
| Example 3-5 | No. 36 | | | 134 | 145 | 103 |
| Example 3-6 | No. 38 | | | 127 | 127 | 103 |
| Example 3-7 | No. 40 | | | 125 | 129 | 102 |
| Example 3-8 | No. 43 | | | 124 | 127 | 103 |
| Example 3-9 | No. 46 | | | 111 | 110 | 103 |
| Example 3-10 | No. 48 | | | 136 | 148 | 105 |
| Example 3-11 | No. 52 | | | 124 | 126 | 104 |
| Example 3-12 | No. 57 | | | 122 | 126 | 103 |
| Example 3-13 | No. 61 | | | 103 | 102 | 102 |
| Comparative example 3-1 | No. 66 | | | 100 | 100 | 100 |
| Comparative example 3-2 | No. 68 | | | 99 | 99 | 98 |
| Comparative example 3-3 | No. 81 | | | 102 | 90 | 100 |
| Comparative example 3-4 | No. 117 | | | 100 | 98 | 97 |
| Comparative example 3-5 | No. 121 | | | 94 | 89 | 99 |
| Example 3-14 | No. 1 | | $Li_4Ti_5O_{12}$ | 120 | 124 | 104 |
| Example 3-15 | No. 19 | | | 119 | 123 | 104 |
| Example 3-16 | No. 26 | | | 112 | 112 | 102 |
| Example 3-17 | No. 28 | | | 117 | 122 | 103 |
| Example 3-18 | No. 36 | | | 117 | 121 | 103 |
| Example 3-19 | No. 38 | | | 113 | 114 | 102 |
| Example 3-20 | No. 40 | | | 113 | 113 | 102 |
| Example 3-21 | No. 43 | | | 111 | 112 | 103 |
| Example 3-22 | No. 46 | | | 105 | 103 | 102 |
| Example 3-23 | No. 48 | | | 117 | 122 | 104 |
| Example 3-24 | No. 52 | | | 112 | 111 | 103 |
| Example 3-25 | No. 57 | | | 111 | 112 | 103 |
| Example 3-26 | No. 61 | | | 102 | 102 | 103 |
| Comparative example 3-6 | No. 66 | | | 100 | 100 | 100 |
| Comparative example 3-7 | No. 68 | | | 100 | 98 | 97 |
| Comparative example 3-8 | No. 81 | | | 101 | 94 | 98 |
| Comparative example 3-9 | No. 117 | | | 99 | 100 | 97 |

TABLE 7-continued

|  | Electrolyte solution No. | Positive electrode Active material | Negative electrode Active material | Discharge capacity maintenance* [%] After 200 cycles | Remaining capacity proportion* [%] | Average discharge voltage* [%] |
|---|---|---|---|---|---|---|
| Comparative example 3-10 | No. 121 |  |  | 94 | 94 | 99 |
| Example 3-27 | No. 1 |  | Graphite | 131 | 144 | 105 |
| Example 3-28 | No. 19 |  | (containing | 130 | 143 | 104 |
| Example 3-29 | No. 26 |  | silicon) | 120 | 123 | 103 |
| Example 3-30 | No. 28 |  |  | 129 | 140 | 103 |
| Example 3-31 | No. 36 |  |  | 130 | 140 | 103 |
| Example 3-32 | No. 38 |  |  | 122 | 122 | 102 |
| Example 3-33 | No. 40 |  |  | 121 | 121 | 102 |
| Example 3-34 | No. 43 |  |  | 120 | 122 | 103 |
| Example 3-35 | No. 46 |  |  | 105 | 106 | 103 |
| Example 3-36 | No. 48 |  |  | 130 | 142 | 103 |
| Example 3-37 | No. 52 |  |  | 120 | 121 | 104 |
| Example 3-38 | No. 57 |  |  | 117 | 120 | 102 |
| Example 3-39 | No. 61 |  |  | 102 | 101 | 102 |
| Comparative example 3-11 | No. 66 |  |  | 100 | 100 | 100 |
| Comparative example 3-12 | No. 68 |  |  | 98 | 97 | 98 |
| Comparative example 3-13 | No. 81 |  |  | 102 | 88 | 98 |
| Comparative example 3-14 | No. 117 |  |  | 98 | 99 | 96 |
| Comparative example 3-15 | No. 121 |  |  | 95 | 92 | 100 |

*Relative value in each corresponding battery configuration, when the value of Comparative example wherein Electrolyte solution No. 66 was used is designated as 100.

TABLE 8

|  | Electrolyte solution No. | Positive electrode Active material | Negative electrode Active material | Discharge capacity maintenance* [%] After 200 cycles | Remaining capacity proportion* [%] | Average discharge voltage* [%] |
|---|---|---|---|---|---|---|
| Example 3-40 | No. 1 | LiCoO$_2$ | Hard | 128 | 140 | 104 |
| Example 3-41 | No. 19 |  | carbon | 127 | 139 | 104 |
| Example 3-42 | No. 26 |  |  | 115 | 119 | 102 |
| Example 3-43 | No. 28 |  |  | 125 | 135 | 103 |
| Example 3-44 | No. 36 |  |  | 124 | 135 | 103 |
| Example 3-45 | No. 38 |  |  | 117 | 118 | 103 |
| Example 3-46 | No. 40 |  |  | 115 | 118 | 102 |
| Example 3-47 | No. 43 |  |  | 115 | 118 | 102 |
| Example 3-48 | No. 46 |  |  | 105 | 104 | 103 |
| Example 3-49 | No. 48 |  |  | 125 | 138 | 104 |
| Example 3-50 | No. 52 |  |  | 114 | 117 | 103 |
| Example 3-51 | No. 57 |  |  | 113 | 115 | 102 |
| Example 3-52 | No. 61 |  |  | 101 | 101 | 102 |
| Comparative example 3-16 | No. 66 |  |  | 100 | 100 | 100 |
| Comparative example 3-17 | No. 68 |  |  | 98 | 99 | 98 |
| Comparative example 3-18 | No. 81 |  |  | 103 | 93 | 99 |
| Comparative example 3-19 | No. 117 |  |  | 98 | 99 | 97 |
| Comparative example 3-20 | No. 121 |  |  | 97 | 92 | 100 |

*Relative value in each corresponding battery configuration, when the value of Comparative example wherein Electrolyte solution No. 66 was used is designated as 100.

Examples 4-1 to 4-39 and Comparative Examples 4-1 to 4-15

In Examples 4-1 to 4-39 and Comparative examples 4-1 to 4-15, as shown in Table 9, the electrolyte solutions for non-aqueous electrolyte batteries were prepared, cells were prepared, and then the batteries were evaluated in the same manner as in Example 1-1, except that the kinds of the positive electrode bodies and the kinds of the electrolyte solutions were changed. In this case, in Examples 4-1 to 4-13 and Comparative examples 4-1 to 4-5 wherein the positive electrode active material is LiNi$_{0.8}$Co$_{0.15}$Al$_{0.05}$O$_2$, the positive electrode body was prepared by mixing 90% by mass of LiNi$_{0.8}$Co$_{0.15}$Al$_{0.05}$O$_2$ powder with 5% by mass of PVDF as a binder and 5% by mass of acetylene black as a conductive additive, to which N-methylpyrrolidone was added, applying the thus obtained paste onto an aluminum foil, and then drying it. The charge end voltage and the discharge end voltage when the resultant batteries were evaluated were 4.3 V and 3.0 V, respectively. In Examples 4-14 to 4-26 and Comparative examples 4-6 to 4-10 wherein the positive electrode active material is LiMn$_2$O$_4$, the positive electrode body was prepared by mixing 90% by mass of LiMn$_2$O$_4$ powder with 5% by mass of PVDF as a binder and 5% by mass of acetylene black as a conductive additive, to which N-methylpyrrolidone was added, applying the thus obtained paste onto an aluminum foil, and then drying it. The charge end voltage and the discharge end voltage when the resultant batteries were evaluated were 4.2 V and 3.0 V, respectively. In Examples 4-27 to 4-39 and Comparative examples 4-11 to 4-15 wherein the positive electrode active material is LiFePO$_4$, the positive electrode body was prepared by mixing 90% by mass of LiFePO$_4$ powder coated with amorphous carbon, with 5% by mass of PVDF as a binder and 5% by mass of acetylene black as a conductive additive, to which N-methylpyrrolidone was added, applying the thus obtained paste onto an aluminum foil, and then drying it. The charge end voltage and the discharge end voltage when the resultant batteries were evaluated were 4.2 V and 2.5 V, respectively. The evaluation results of a high-temperature cycle characteristic, high-temperature storage characteristic and low-temperature output characteristic are shown in Table 9. The evaluation results (the values of discharge capacity maintenance % after 200 cycles, the values of remaining capacity proportion, the values of average discharge voltage) in Table 9 are values relative to the evaluation results in the Comparative examples using the electrolyte solution No.66 designated as 100 in respect of each electrode constitution.

TABLE 9

| | Electrolyte solution No. | Positive electrode Active material | Negative electrode Active material | Discharge capacity maintenance* [%] After 200 cycles | Remaining capacity proportion* [%] | Average discharge voltage* [%] |
|---|---|---|---|---|---|---|
| Example 4-1 | No. 1 | LiNi$_{0.8}$Co$_{0.15}$Al$_{0.05}$O$_2$ | Graphite | 134 | 147 | 106 |
| Example 4-2 | No. 19 | | | 133 | 145 | 105 |
| Example 4-3 | No. 26 | | | 121 | 123 | 104 |
| Example 4-4 | No. 28 | | | 130 | 141 | 104 |
| Example 4-5 | No. 36 | | | 130 | 140 | 103 |
| Example 4-6 | No. 38 | | | 121 | 123 | 103 |
| Example 4-7 | No. 40 | | | 121 | 125 | 103 |
| Example 4-8 | No. 43 | | | 120 | 123 | 102 |
| Example 4-9 | No. 46 | | | 109 | 107 | 103 |
| Example 4-10 | No. 48 | | | 131 | 144 | 103 |
| Example 4-11 | No. 52 | | | 120 | 122 | 104 |
| Example 4-12 | No. 57 | | | 117 | 122 | 103 |
| Example 4-13 | No. 61 | | | 103 | 103 | 103 |
| Comparative example 4-1 | No. 66 | | | 100 | 100 | 100 |
| Comparative example 4-2 | No. 68 | | | 99 | 99 | 97 |
| Comparative example 4-3 | No. 81 | | | 101 | 91 | 100 |
| Comparative example 4-4 | No. 117 | | | 99 | 100 | 97 |
| Comparative example 4-5 | No. 121 | | | 94 | 88 | 100 |
| Example 4-14 | No. 1 | LiMn$_2$O$_4$ | Graphite | 130 | 135 | 105 |
| Example 4-15 | No. 19 | | | 128 | 133 | 104 |
| Example 4-16 | No. 26 | | | 118 | 115 | 103 |
| Example 4-17 | No. 28 | | | 126 | 131 | 103 |
| Example 4-18 | No. 36 | | | 125 | 131 | 102 |
| Example 4-19 | No. 38 | | | 119 | 113 | 102 |
| Example 4-20 | No. 40 | | | 117 | 115 | 103 |
| Example 4-21 | No. 43 | | | 118 | 114 | 103 |
| Example 4-22 | No. 46 | | | 108 | 108 | 103 |
| Example 4-23 | No. 48 | | | 129 | 134 | 104 |
| Example 4-24 | No. 52 | | | 117 | 112 | 103 |
| Example 4-25 | No. 57 | | | 115 | 113 | 102 |
| Example 4-26 | No. 61 | | | 104 | 105 | 102 |
| Comparative example 4-6 | No. 66 | | | 100 | 100 | 100 |
| Comparative example 4-7 | No. 68 | | | 98 | 99 | 98 |
| Comparative example 4-8 | No. 81 | | | 102 | 92 | 99 |
| Comparative example 4-9 | No. 117 | | | 100 | 98 | 96 |
| Comparative example 4-10 | No. 121 | | | 95 | 93 | 100 |
| Example 4-27 | No. 1 | LiFePO$_4$ | Graphite | 120 | 126 | 103 |
| Example 4-28 | No. 19 | | | 118 | 125 | 103 |
| Example 4-29 | No. 26 | | | 114 | 114 | 103 |
| Example 4-30 | No. 28 | | | 117 | 123 | 102 |
| Example 4-31 | No. 36 | | | 117 | 122 | 102 |
| Example 4-32 | No. 38 | | | 113 | 114 | 102 |
| Example 4-33 | No. 40 | | | 112 | 115 | 102 |
| Example 4-34 | No. 43 | | | 113 | 116 | 102 |
| Example 4-35 | No. 46 | | | 110 | 108 | 102 |
| Example 4-36 | No. 48 | | | 119 | 123 | 103 |
| Example 4-37 | No. 52 | | | 113 | 114 | 103 |
| Example 4-38 | No. 57 | | | 111 | 114 | 102 |

TABLE 9-continued

| | Electrolyte solution No. | Positive electrode Active material | Negative electrode Active material | Discharge capacity maintenance* [%] After 200 cycles | Remaining capacity proportion* [%] | Average discharge voltage* [%] |
|---|---|---|---|---|---|---|
| Example 4-39 | No. 61 | | | 104 | 103 | 102 |
| Comparative example 4-11 | No. 66 | | | 100 | 100 | 100 |
| Comparative example 4-12 | No. 68 | | | 100 | 98 | 99 |
| Comparative example 4-13 | No. 81 | | | 103 | 96 | 100 |
| Comparative example 4-14 | No. 117 | | | 98 | 98 | 98 |
| Comparative example 4-15 | No. 121 | | | 96 | 94 | 99 |

*Relative value in each corresponding battery configuration, when the value of Comparative example wherein Electrolyte solution No. 66 was used is designated as 100.

As shown in the above, the results confirm that a high-temperature cycle characteristic, high-temperature storage characteristic, and low-temperature output characteristic were improved in any of Examples where the electrolyte solution for a non-aqueous electrolyte battery of the present invention was used and the negative electrode active material is any of $Li_4Ti_5O_{12}$, graphite (containing silicon) and hard carbon, as compared with the corresponding Comparative examples. Thus, it was shown that the use of the electrolyte solution for a non-aqueous electrolyte battery of the present invention provides an excellent high-temperature cycle characteristic, excellent high-temperature storage characteristic, and excellent low-temperature output characteristic, regardless of the kinds of the negative electrode active materials.

The results also confirm that a high-temperature cycle characteristic, high-temperature storage characteristic and low-temperature output characteristic were improved in any of Examples where the electrolyte solution for a non-aqueous electrolyte battery of the present invention was used and the positive electrode active material is any of $LiCoO_2$, $LiNi_{0.8}Co_{0.15}Al_{0.05}O_2$, $LiMn_2O_4$ and $LiFePO_4$, as compared with the corresponding Comparative examples. Thus, it was shown that the use of the electrolyte solution for a non-aqueous electrolyte battery of the present invention provides an excellent high-temperature cycle characteristic, excellent high-temperature storage characteristic and excellent low-temperature output characteristic, regardless of the kinds of the positive electrode active materials.

Example 5-1

A mixed solvent containing ethylene carbonate and diethyl carbonate at a volume ratio of 1:1 was used as a non-aqueous solvent. $NaPF_6$ as a solute was dissolved in the solvent so as to achieve a concentration of 1.0 mol/L. Then, the compound No.2 as the first compound was added to the resultant solution, so as to achieve a concentration of 0.5% by mass and a sodium salt of the compound No.15 as the second compound was added to the resultant solution so as to achieve a concentration of 1.0% by mass, followed by stirring, to prepare an electrolyte solution No.139. Table 10 shows the conditions for preparation of the electrolyte solution No.139.

Cells were produced using this electrolyte solution in the same manner as in Example 1-1, except that $NaFe_{0.5}Co_{0.5}O_2$ was used as a positive electrode material and hard carbon was used as a negative electrode material. The resultant batteries were evaluated for a high-temperature cycle characteristic, high-temperature storage characteristic and low-temperature output characteristic in the same manner as in Example 1-1. In this case, the positive electrode body wherein the positive electrode active material is $NaFe_{0.5}Co_{0.5}O_2$ was prepared by mixing 90% by mass of $NaFe_{0.5}Co_{0.5}O_2$ powder, 5% by mass of PVDF as a binder, and 5% by mass of acetylene black as a conductive additive, to which N-methylpyrrolidone was added, applying the thus obtained paste onto an aluminum foil, and then drying it. The charge end voltage and the discharge end voltage when the batteries were evaluated were 3.8 V and 1.5 V, respectively. The evaluation results are shown in Table 11.

Examples 5-2 to 5-13 and Comparative Examples 5-1 to 5-6

In Examples 5-2 to 5-13 and Comparative examples 5-1 to 5-6, as shown in Table 10, electrolyte solutions for non-aqueous electrolyte batteries were prepared, cells were prepared, and then the batteries were evaluated in the same manner as in Example 5-1, except that kinds of the first compounds and second compounds were changed. The evaluation results of a high-temperature cycle characteristic, high-temperature storage characteristic and low-temperature output characteristic are shown in Table 11. The evaluation results (the values of discharge capacity maintenance % after 200 cycles, the values of remaining capacity proportion, the values of average discharge voltage) in Table 11 are values relative to the evaluation results in Comparative example 5-1 designated as 100.

TABLE 10

| | First compound | | Second compound | | |
|---|---|---|---|---|---|
| | Compound No. | Concentration [% by mass] | Compound No. | Counter cation | Concentration [% by mass] |
| Electrolyte solution No. 139 | No. 2 | 0.5 | No. 15 | Na+ | 1.0 |
| Electrolyte solution No. 140 | No. 7 | 0.5 | | | 1.0 |
| Electrolyte solution No. 141 | No. 2 | 0.5 | No. 14 | | 1.0 |
| Electrolyte solution No. 142 | | 0.5 | No. 17 | | 1.0 |

TABLE 10-continued

| | First compound | | Second compound | | |
|---|---|---|---|---|---|
| | Compound No. | Concentration [% by mass] | Compound No. | Counter cation | Concentration [% by mass] |
| Electrolyte solution No. 143 | | 0.5 | No. 25 | | 1.0 |
| Electrolyte solution No. 144 | | 0.5 | No. 27 | | 1.0 |
| Electrolyte solution No. 145 | | 0.5 | No. 29 | | 1.0 |
| Electrolyte solution No. 146 | | 0.5 | No. 32 | | 1.0 |
| Electrolyte solution No. 147 | | 0.5 | No. 35 | | 1.0 |
| Electrolyte solution No. 148 | | 0.5 | No. 37 | 2Na$^+$ | 1.0 |
| Electrolyte solution No. 149 | | 0.5 | No. 41 | | 1.0 |
| Electrolyte solution No. 150 | | 0.5 | No. 46 | | 1.0 |
| Electrolyte solution No. 151 | | 0.5 | No. 50 | | 1.0 |
| Electrolyte solution No. 152 | None | — | None | | — |
| Electrolyte solution No. 153 | No. 2 | 0.5 | | | — |
| Electrolyte solution No. 154 | None | — | No. 15 | Na$^+$ | 1.0 |
| Electrolyte solution No. 155 | No. 51 | 0.5 | | | 1.0 |
| Electrolyte solution No. 156 | No. 2 | 0.5 | No. 55 | | 1.0 |
| Electrolyte solution No. 157 | | 0.5 | No. 59 | | 1.0 |

TABLE 11

| | Electrolyte solution No. | Positive electrode Active material | Negative electrode Active material | Discharge capacity maintenance* [%] After 200 cycles | Remaining capacity proportion* [%] | Average discharge voltage* [%] |
|---|---|---|---|---|---|---|
| Example 5-1 | No. 139 | NaFe$_{0.5}$Co$_{0.5}$O$_2$ | Hard carbon | 135 | 140 | 104 |
| Example 5-2 | No. 140 | | | 134 | 138 | 104 |
| Example 5-3 | No. 141 | | | 123 | 119 | 103 |
| Example 5-4 | No. 142 | | | 131 | 138 | 103 |
| Example 5-5 | No. 143 | | | 132 | 136 | 103 |
| Example 5-6 | No. 144 | | | 124 | 118 | 103 |
| Example 5-7 | No. 145 | | | 123 | 120 | 103 |
| Example 5-8 | No. 146 | | | 122 | 120 | 103 |
| Example 5-9 | No. 147 | | | 110 | 108 | 102 |
| Example 5-10 | No. 148 | | | 133 | 139 | 103 |
| Example 5-11 | No. 149 | | | 122 | 117 | 103 |
| Example 5-12 | No. 150 | | | 120 | 118 | 103 |
| Example 5-13 | No. 151 | | | 102 | 103 | 102 |
| Comparative example 5-1 | No. 152 | | | 100 | 100 | 100 |
| Comparative example 5-2 | No. 153 | | | 99 | 98 | 98 |
| Comparative example 5-3 | No. 154 | | | 102 | 94 | 99 |
| Comparative example 5-4 | No. 155 | | | 99 | 98 | 97 |
| Comparative example 5-5 | No. 156 | | | 93 | 90 | 99 |
| Comparative example 5-6 | No. 157 | | | 95 | 92 | 98 |

*Relative value when the result of Comparative example 5-1 is designated as 100.

From the above results, even in a sodium ion battery, it was confirmed that a high-temperature cycle characteristic, high-temperature storage characteristic and low-temperature output characteristic were improved by using the first compound and the second compound in combination, as compared with Comparative example 5-2 wherein the first compound was used alone. Similarly, it was also confirmed that a high-temperature cycle characteristic, high-temperature storage characteristic and low-temperature output characteristic were improved as compared with Comparative example 5-3 wherein the second compound was used alone. As shown in the case of Comparative example 5-4 wherein $R^2$ of the first compound represented by general formula (1) is not a linear or branched $C_{1-10}$ alkyl group ($R^2$ in Comparative example 5-4 contains a fluorine group), a low-temperature output characteristic was decreased and no improvement was confirmed in a high-temperature cycle characteristic or high-temperature storage characteristic.

As shown in the case of Comparative example 5-5 wherein the second compound contained neither a P—F bond nor an S—F bond, no improvement was confirmed in a high-temperature cycle characteristic, high-temperature storage characteristic or low-temperature output characteristic.

As shown in the case of Comparative example 5-6 wherein the second compound contains a P—F bond but has a structure where the substituent is bonded to a P atom is not a hydrocarbon group containing an intervening oxygen atom (e.g., an alkoxy group) but a hydrocarbon group containing no intervening oxygen atom (i.e., an alkyl group), a low-temperature output characteristic was decreased and no improvement was confirmed in a high-temperature cycle characteristic or high-temperature storage characteristic.

The invention claimed is:

1. An electrolyte solution for a non-aqueous electrolyte battery, comprising at least a non-aqueous solvent, a solute, at least one silane compound represented by the following formula (1) as a first compound, and at least one compound selected from the group consisting of fluorine-containing compounds represented by the following formulae (4) to (9) as a second compound:

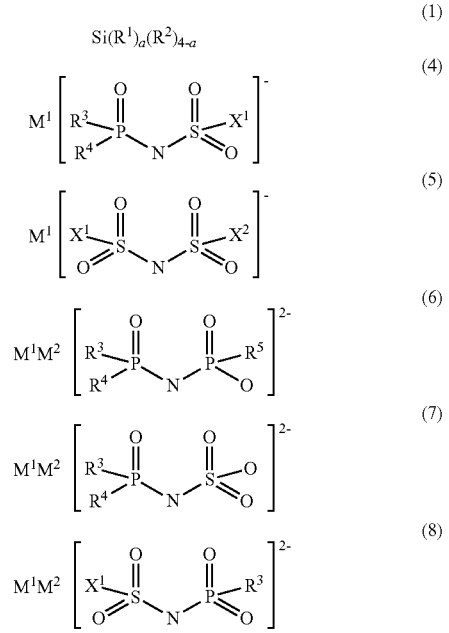

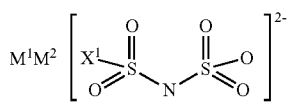

wherein,
in formula (1),
$R^1$ each independently represents a group having a carbon-carbon unsaturated bond,
$R^2$ each independently represents a linear or branched $C_{1-10}$ alkyl group, which may optionally contain a fluorine atom and/or an oxygen atom, with the proviso that when $R^2$ contains an oxygen atom, the alkyl group of $R^2$ is a structure other than an alkoxy group, and
a is 2 to 4;
in formulae (4) and (6) to (8),
$R^3$ to $R^5$ each independently represents a fluorine atom or an organic group selected from among a linear or branched $C_{1-10}$ alkoxy group, a $C_{2-10}$ alkenyloxy group, a $C_{2-10}$ alkynyloxy group, a $C_{3-10}$ cycloalkoxy group, a $C_{3-10}$ cycloalkenyloxy group and a $C_{6-10}$ aryloxy group, wherein a fluorine atom, an oxygen atom, or an unsaturated bond may optionally be present in the organic group;
in formulae (4), (5), (8), and (9),
$X^1$ and $X^2$ each independently represents a fluorine atom or an organic group selected from a linear or branched $C_{1-10}$ alkyl group, a $C_{2-10}$ alkenyl group, a $C_{2-10}$ alkynyl group, a $C_{3-10}$ cycloalkyl group, a $C_{3-10}$ cycloalkenyl group, a $C_{6-10}$ aryl group, a linear or branched $C_{1-10}$ alkoxy group, a $C_{2-10}$ alkenyloxy group, a $C_{2-10}$ alkynyloxy group, a $C_{3-10}$ cycloalkoxy group, a $C_{3-10}$ cycloalkenyloxy group and a $C_{6-10}$ aryloxy group, wherein a fluorine atom, an oxygen atom, or an unsaturated bond may optionally be present in the organic group as well;
wherein formulae (4) to (9) have at least one P—F bond and/or at least one S—F bond; and
wherein $M^1$ and $M^2$ each independently represents a proton, a metal cation or an onium cation.

2. The electrolyte solution for a non-aqueous electrolyte battery according to claim 1, wherein the amount of said first compound to be added ranges from 0.001 to 10.0% by mass relative to the total amount of the electrolyte solution for a non-aqueous electrolyte battery.

3. The electrolyte solution for a non-aqueous electrolyte battery according to claim 1, wherein the amount of said second compound ranges from 0.001 to 10.0% by mass relative to the total amount of the electrolyte solution for a non-aqueous electrolyte battery.

4. The electrolyte solution for a non-aqueous electrolyte battery according to claim 1, wherein the group represented by $R^1$ in said formula (1) each independently represents a group selected from the group consisting of a vinyl group, an allyl group, a 1-propenyl group, a 2-propenyl group, an ethynyl group and a 2-propynyl group.

5. The electrolyte solution for a non-aqueous electrolyte battery according to claim 1, wherein the group represented by $R^2$ in said formula (1) each independently represents a group selected from the group consisting of a methyl group, an ethyl group, a propyl group, a 2,2,2-trifluoroethyl group, a 2,2,3,3-tetrafluoropropyl group, a 1,1,1-trifluoroisopropyl group and a 1,1,1,3,3,3-hexafluoroisopropyl group.

6. The electrolyte solution for a non-aqueous electrolyte battery according to claim 1, wherein $R^3$ to $R^5$ in said formulae (4) and (6) to (8) represent a fluorine atom or an organic group selected from the group consisting of a fluorine-atom-containing linear or branched $C_{1-10}$ alkoxy group, a $C_{2-10}$ alkenyloxy group and a $C_{2-10}$ alkynyloxy group.

7. The electrolyte solution for a non-aqueous electrolyte battery according to claim 6, wherein said alkoxy group is selected from the group consisting of a 2,2,2-trifluoroethoxy group, a 2,2,3,3-tetrafluoropropoxy group, a 1,1,1-trifluoroisopropoxy group and a 1,1,1,3,3,3-hexafluoroisopropoxy group; said alkenyloxy group is selected from the group consisting of a 1-propenyloxy group, a 2-propenyloxy group and a 3-butenyloxy group; and said alkynyloxy group is selected from the group consisting of a 2-propynyloxy group and a 1,1-dimethyl-2-propynyloxy group.

8. The electrolyte solution for a non-aqueous electrolyte battery according to claim 1, wherein $X^1$ and $X^2$ in said formulae (4), (5), (8) and (9) are a fluorine atom or an organic group selected from the group consisting of a linear or branched $C_{1-10}$ alkoxy group, a $C_{2-10}$ alkenyloxy group, and a $C_{2-10}$ alkynyloxy group.

9. The electrolyte solution for a non-aqueous electrolyte battery according to claim 8, wherein said alkoxy group is selected from the group consisting of a methoxy group, an ethoxy group and a propoxy group; said alkenyloxy group is selected from the group consisting of a 1-propenyloxy group, a 2-propenyloxy group and a 3-butenyloxy group; and said alkynyloxy group is selected from the group consisting of a 2-propynyloxy group and a 1,1-dimethyl-2-propynyloxy group.

10. The electrolyte solution for a non-aqueous electrolyte battery according to claim 1, wherein $M^1$ and $M^2$ in said formulae (4) to (9) represent at least one cation selected from the group consisting of a lithium ion, a sodium ion, a potassium ion, a tetraalkylammonium ion and a tetraalkylphosphonium ion.

11. The electrolyte solution for a non-aqueous electrolyte battery according to claim 1, wherein said solute is at least one solute selected from the group consisting of lithium hexafluorophosphate, lithium tetrafluoroborate, lithium bis(trifluoromethanesulfonyl)imide, lithium bis(fluorosulfonyl)imide, lithium bis(difluorophosphoryl)imide, sodium hexafluorophosphate, sodium tetrafluoroborate, sodium bis(trifluoromethanesulfonyl)imide, sodium bis(fluorosulfonyl)imide and sodium bis(difluorophosphoryl)imide.

12. The electrolyte solution for a non-aqueous electrolyte battery according to claim 1, wherein said non-aqueous solvent is at least one non-aqueous solvent selected from the group consisting of a cyclic carbonate, a linear carbonate, a cyclic ester, a linear ester, a cyclic ether, a linear ether, a sulfone compound, a sulfoxide compound and an ionic liquid.

13. A non-aqueous electrolyte battery, comprising at least a positive electrode, a negative electrode, a separator, and the electrolyte solution for a non-aqueous electrolyte battery according to claim 1.

* * * * *